United States Patent [19]
Kriesel

[11] Patent Number: 6,030,363
[45] Date of Patent: Feb. 29, 2000

[54] MEDICAMENT DISPENSER

[75] Inventor: Marshall S. Kriesel, St. Paul, Minn.

[73] Assignee: Science Incorporated, Bloomington, Minn.

[21] Appl. No.: 09/060,858

[22] Filed: Apr. 15, 1998

Related U.S. Application Data

[63] Continuation-in-part of application No. 08/473,650, Jun. 6, 1995, which is a continuation-in-part of application No. 08/349,496, Dec. 2, 1994.

[51] Int. Cl.[7] .................................................. A61M 37/00
[52] U.S. Cl. .......................................................... 604/132
[58] Field of Search .................................... 604/132, 134, 604/135, 131, 184, 185; 128/DIG. 12

[56] References Cited

U.S. PATENT DOCUMENTS

| | | | |
|---|---|---|---|
| 4,209,014 | 6/1980 | Sefton | 604/132 |
| 4,592,745 | 6/1986 | Rex et al. | 604/211 |
| 4,813,937 | 3/1989 | Vaillancourt | 604/131 |
| 5,100,389 | 3/1992 | Vaillancourt | 604/135 |
| 5,478,316 | 12/1995 | Bitdinger et al. | 604/135 |

Primary Examiner—Jeffrey A. Smith
Assistant Examiner—Eduardo C. Robert
Attorney, Agent, or Firm—James E. Brunton

[57] ABSTRACT

An injectable medicament dispenser for use in controllably dispensing fluid medicaments such as insulin, antibiotics, oncolytics and the like from a prefilled container at a uniform rate. The dispenser includes a unique stored energy source in the form of a compressively deformable, polymeric elastomeric member that provides the force necessary to controllably discharge the medicament from the prefilled container which is housed within the body of the device. After having been deformed, the polymeric, elastomeric member will return to its starting configuration in a highly predictable manner.

56 Claims, 28 Drawing Sheets

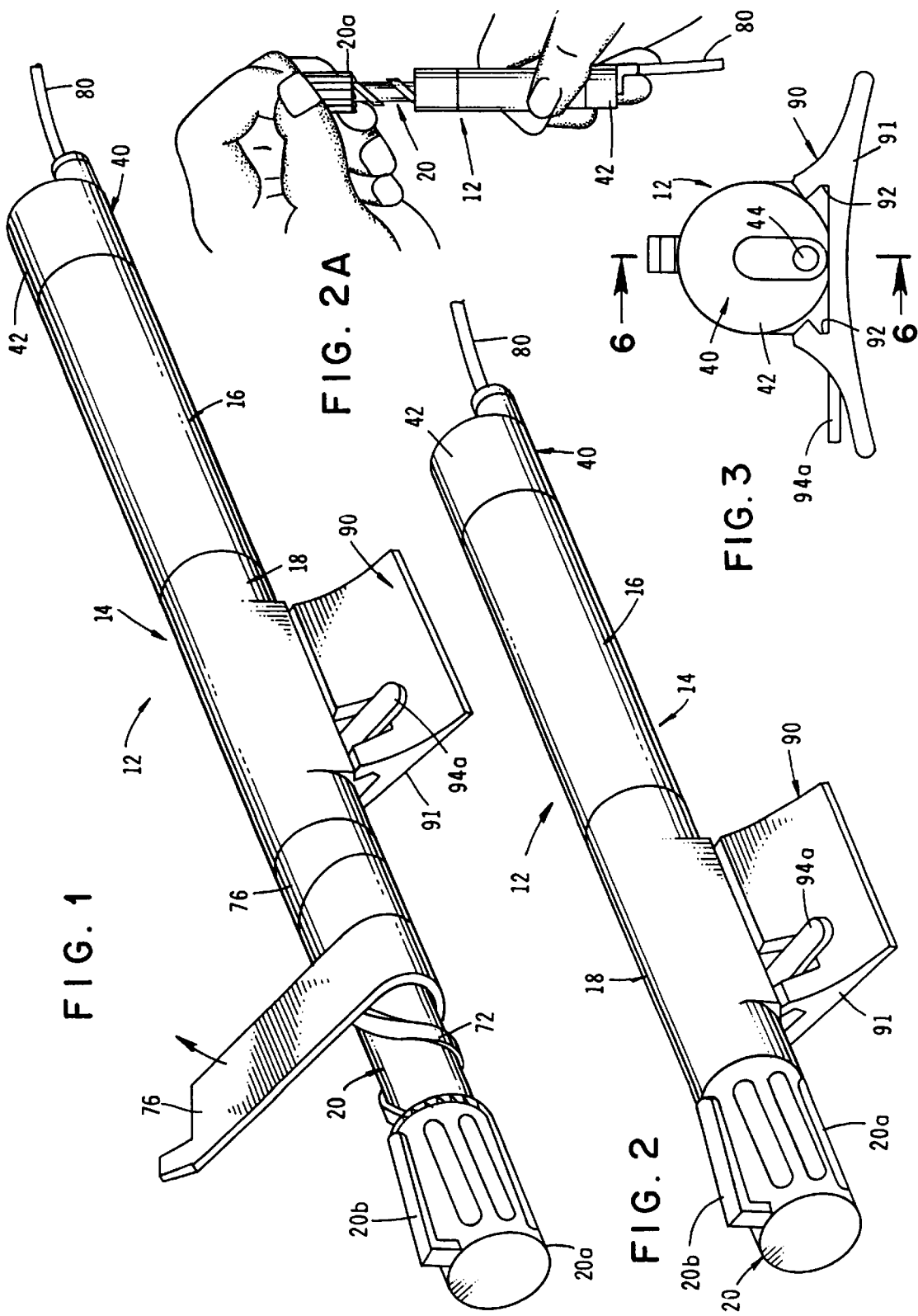

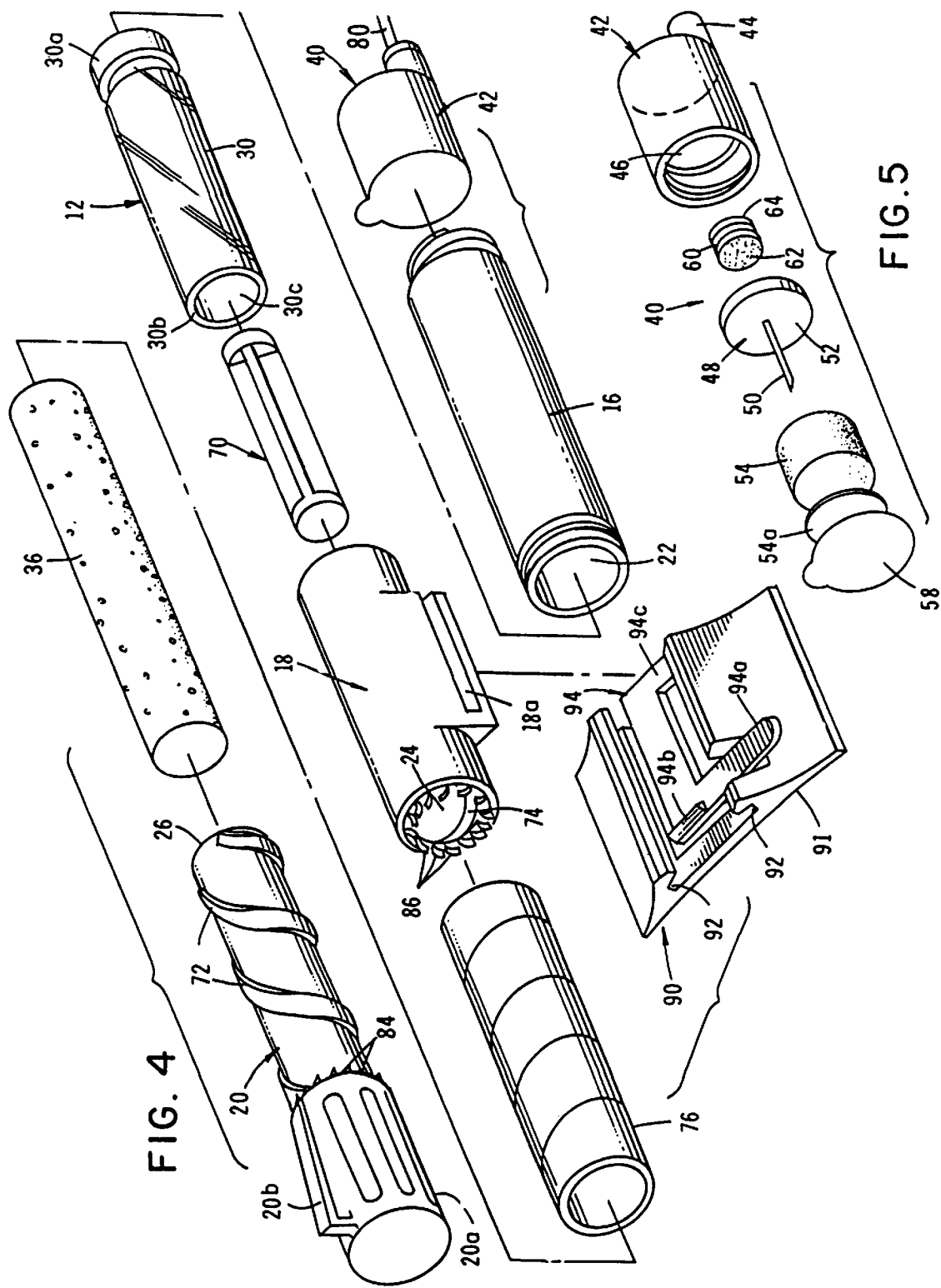

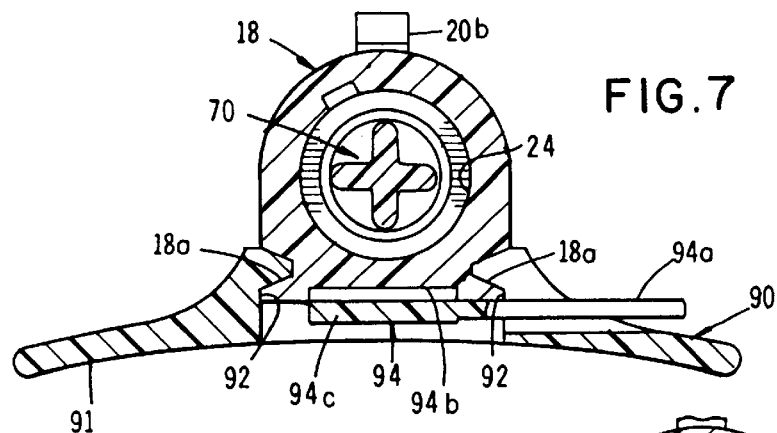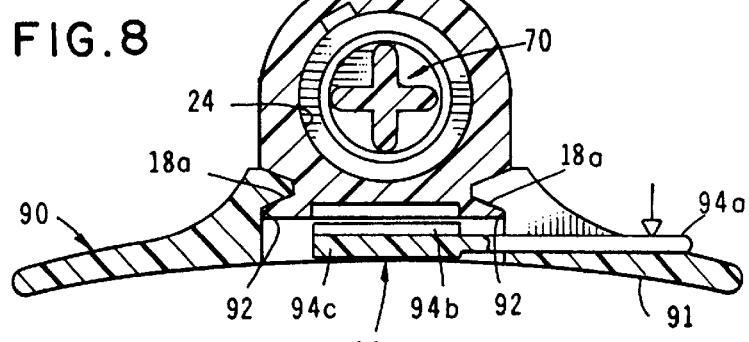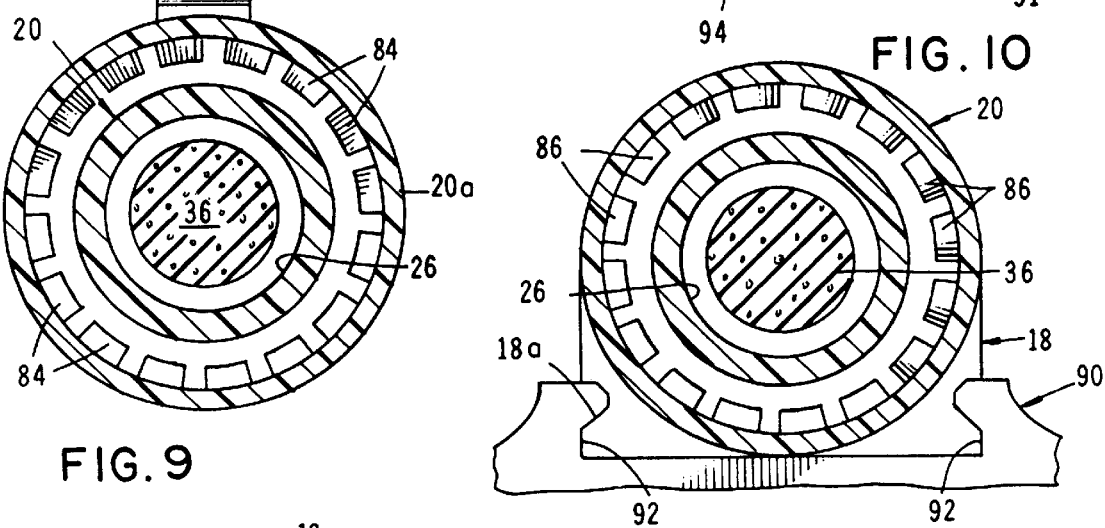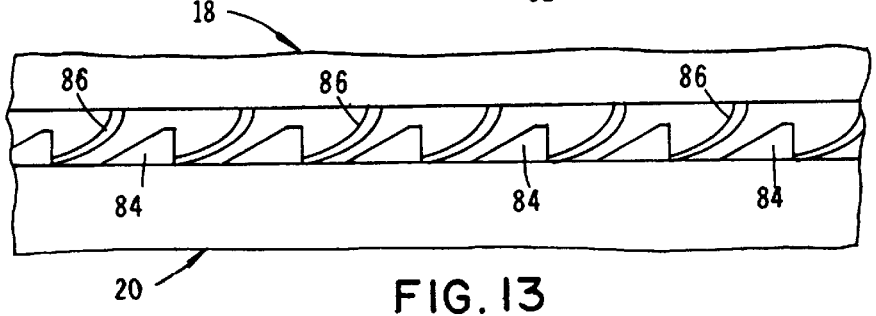

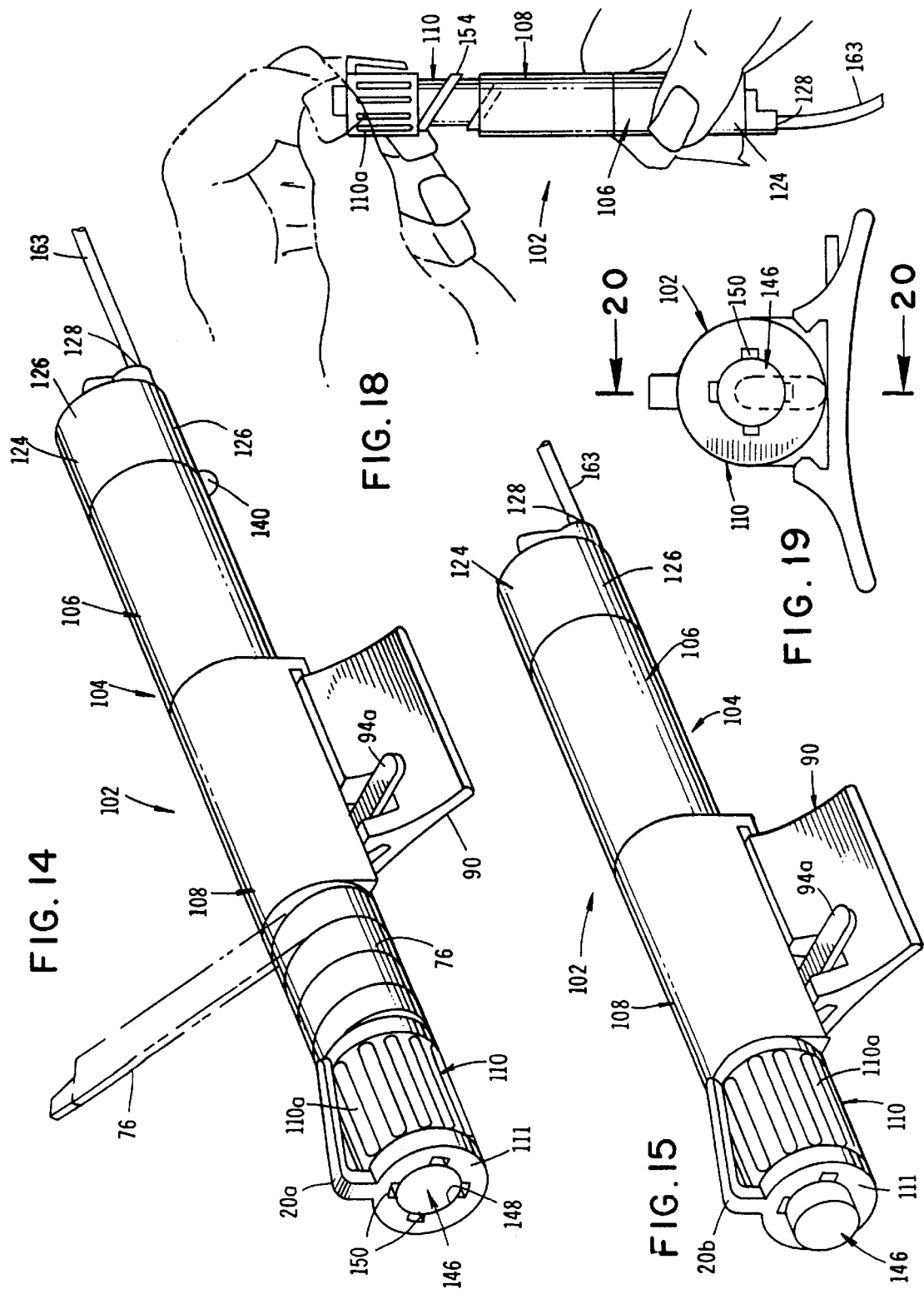

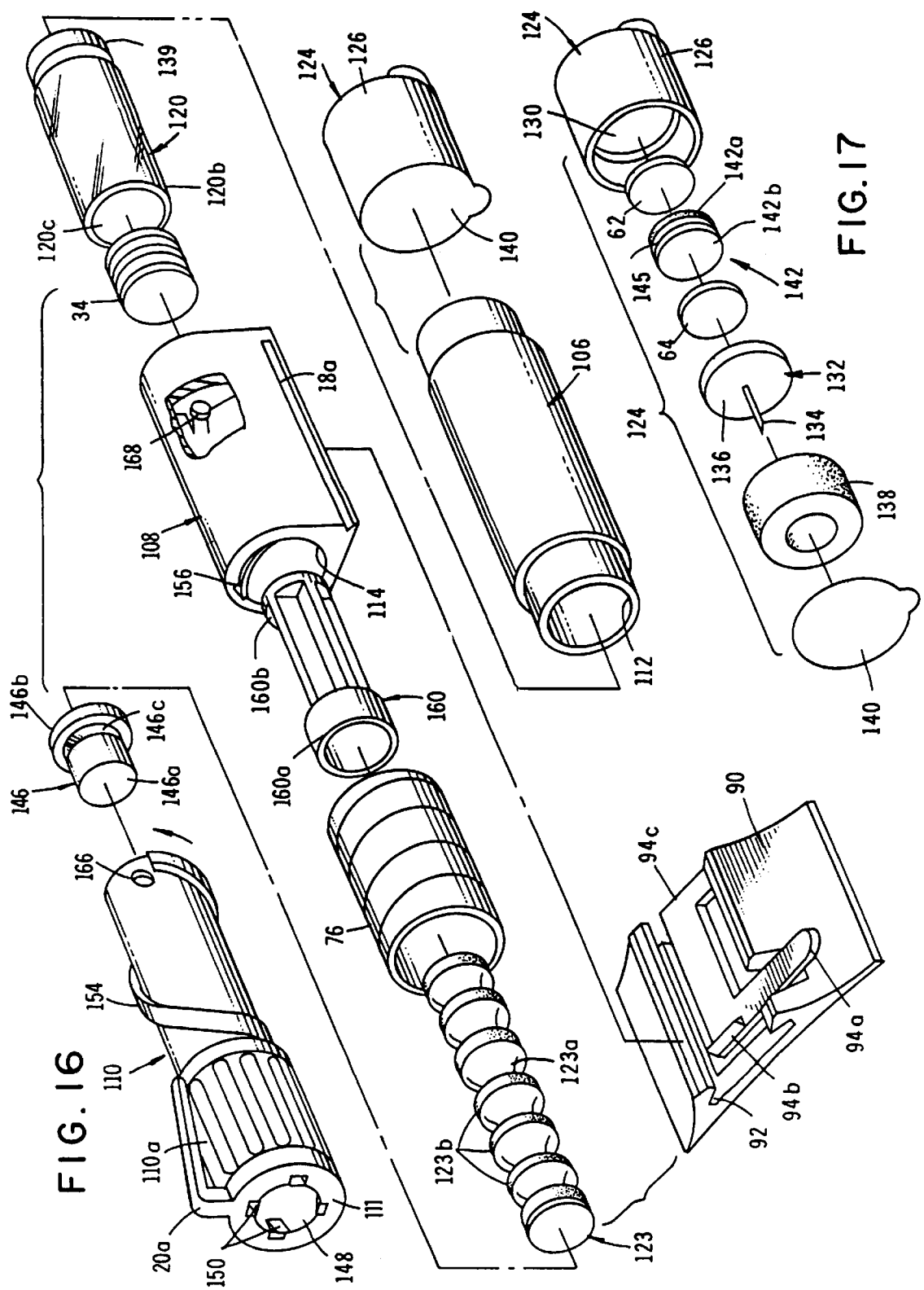

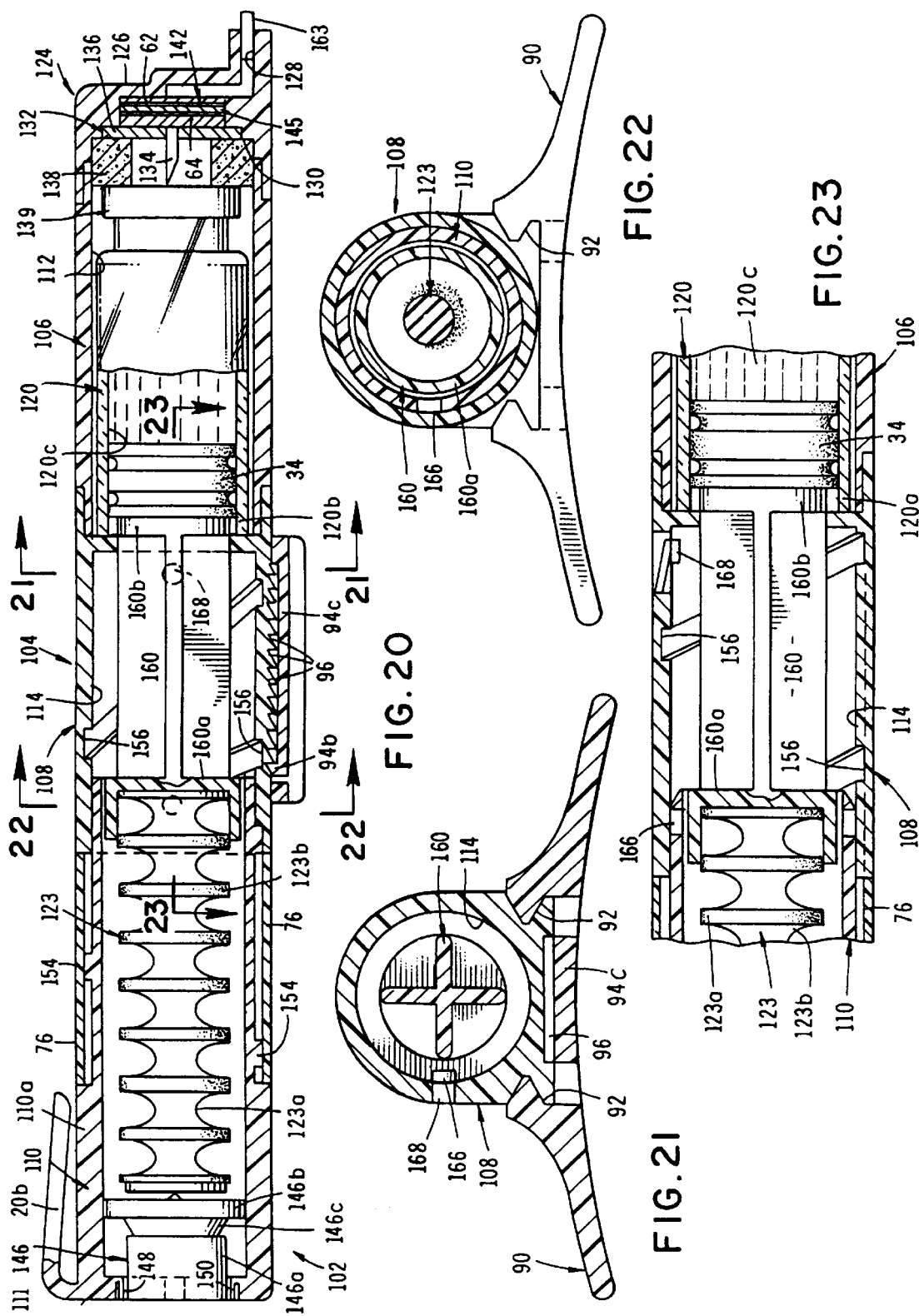

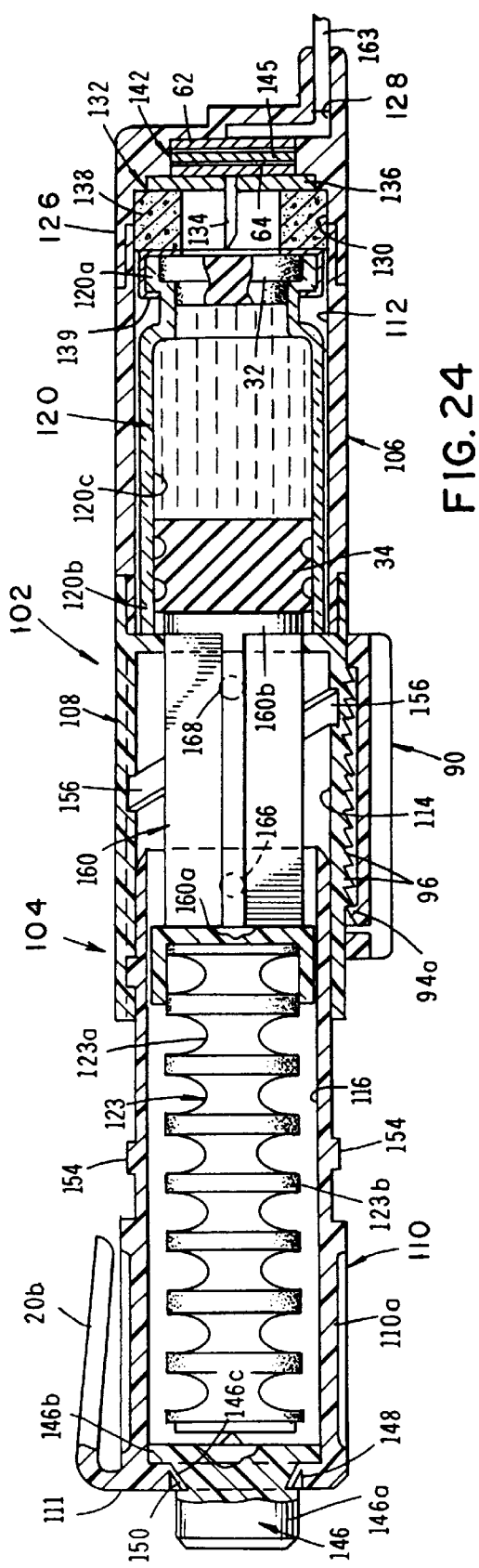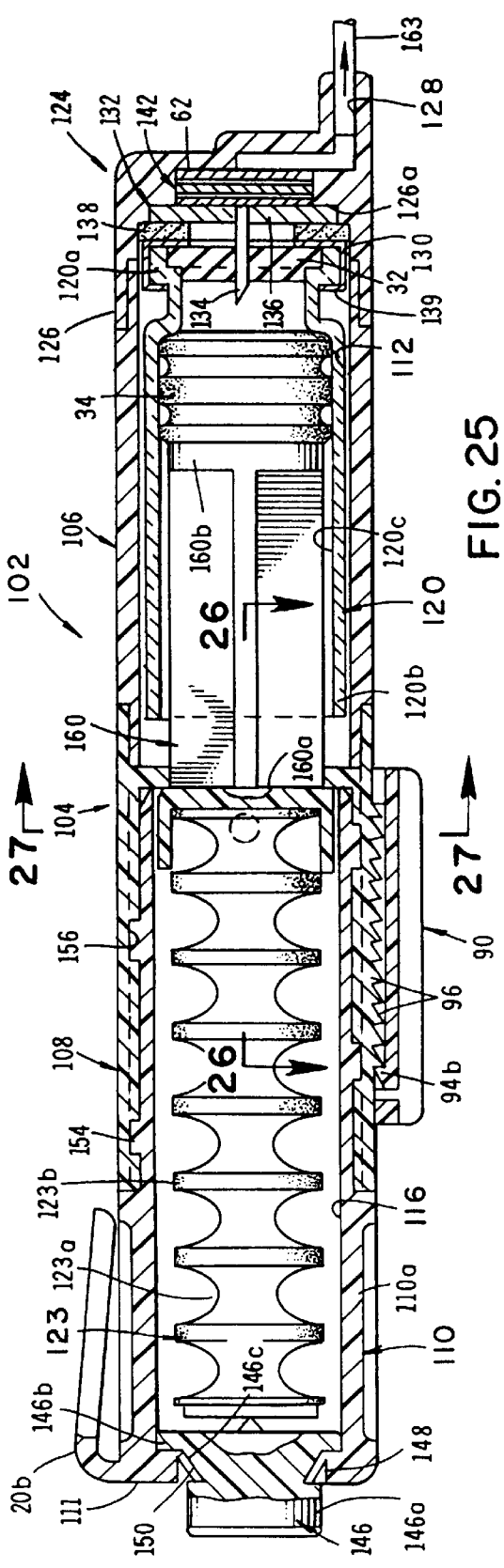

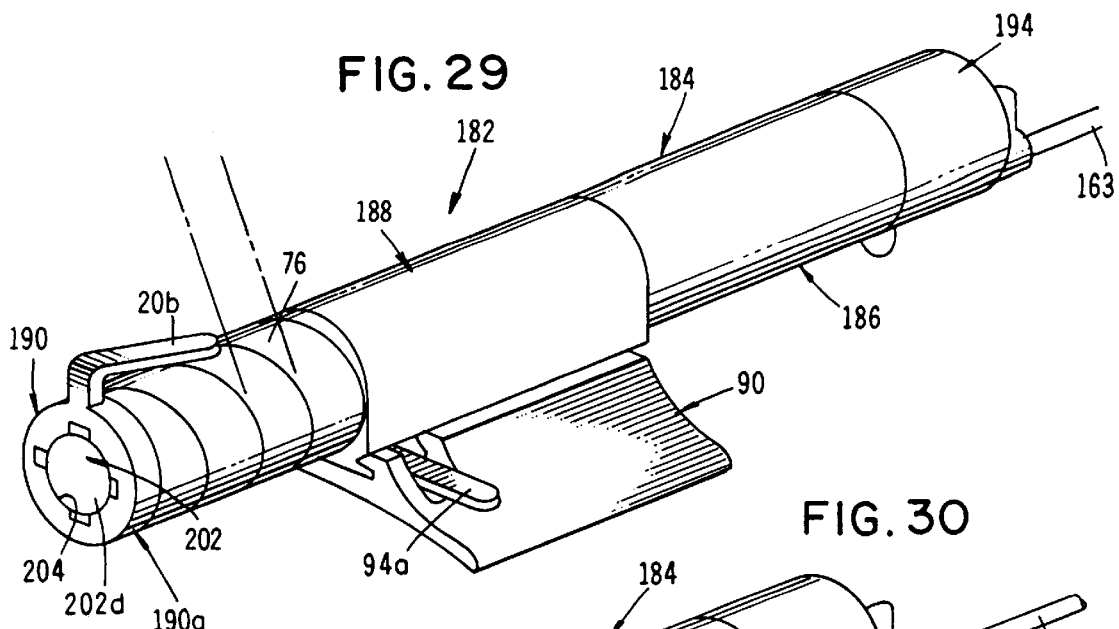
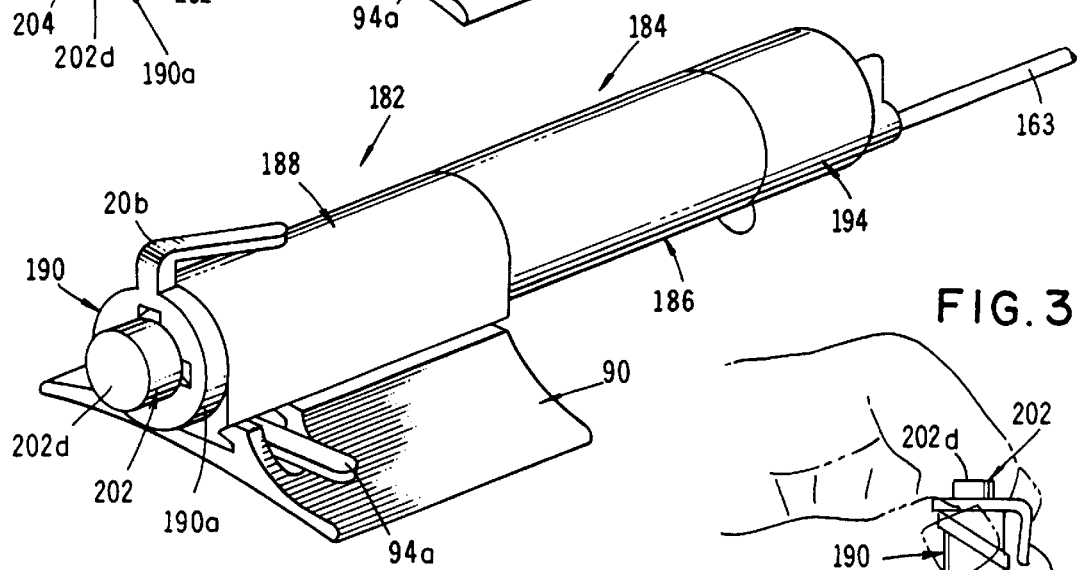
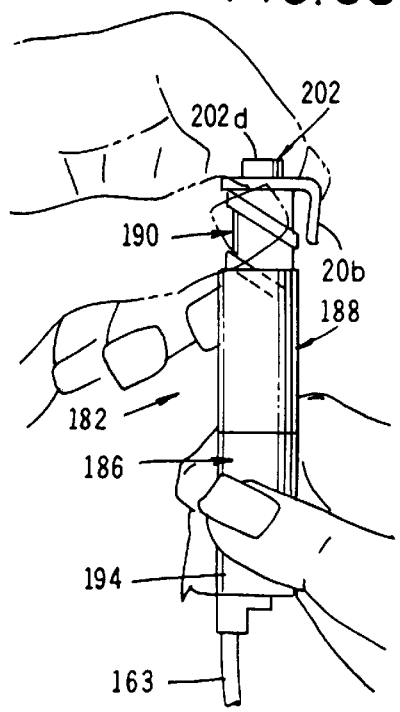
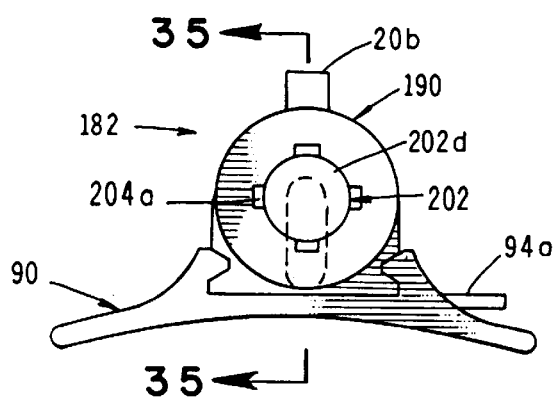

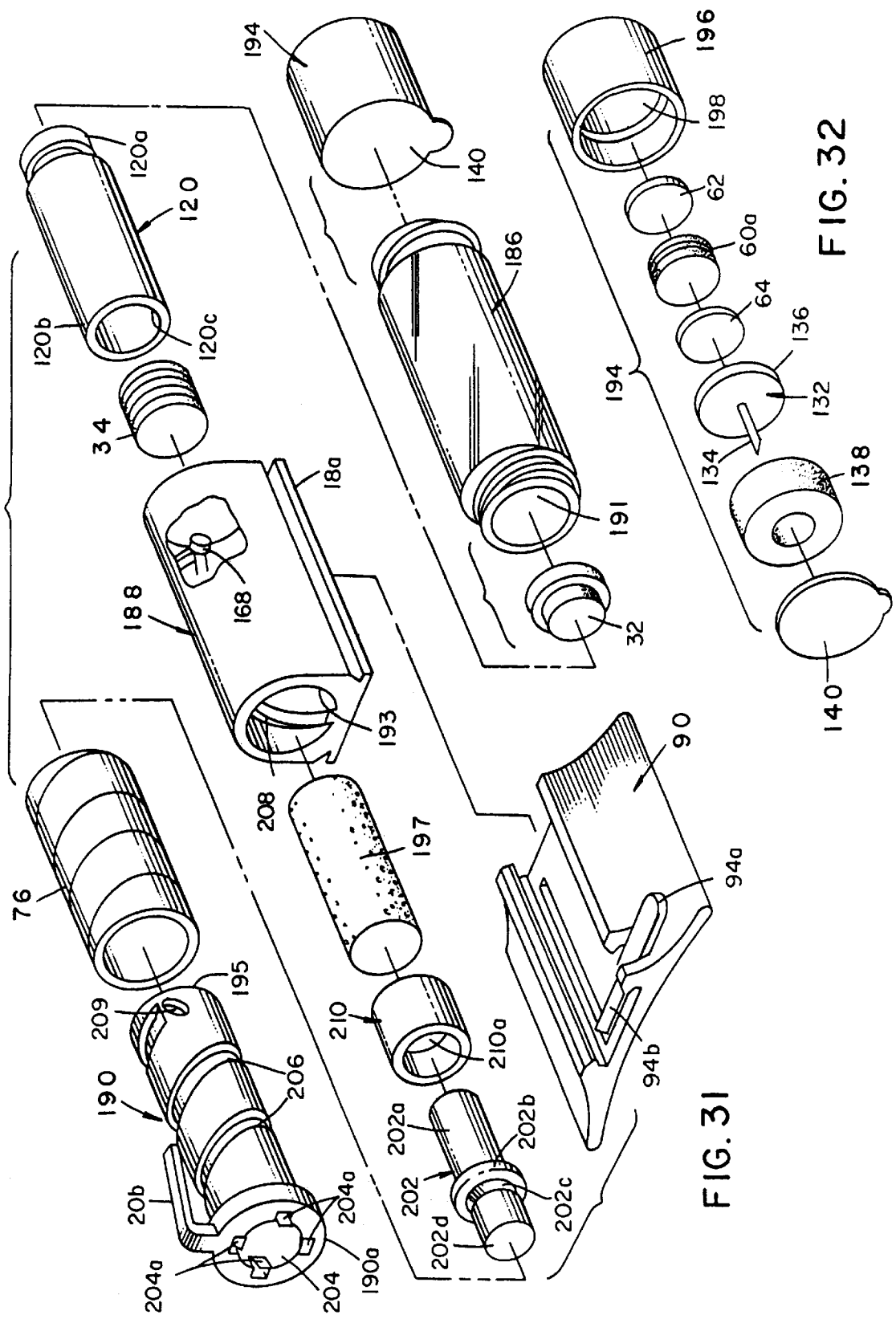

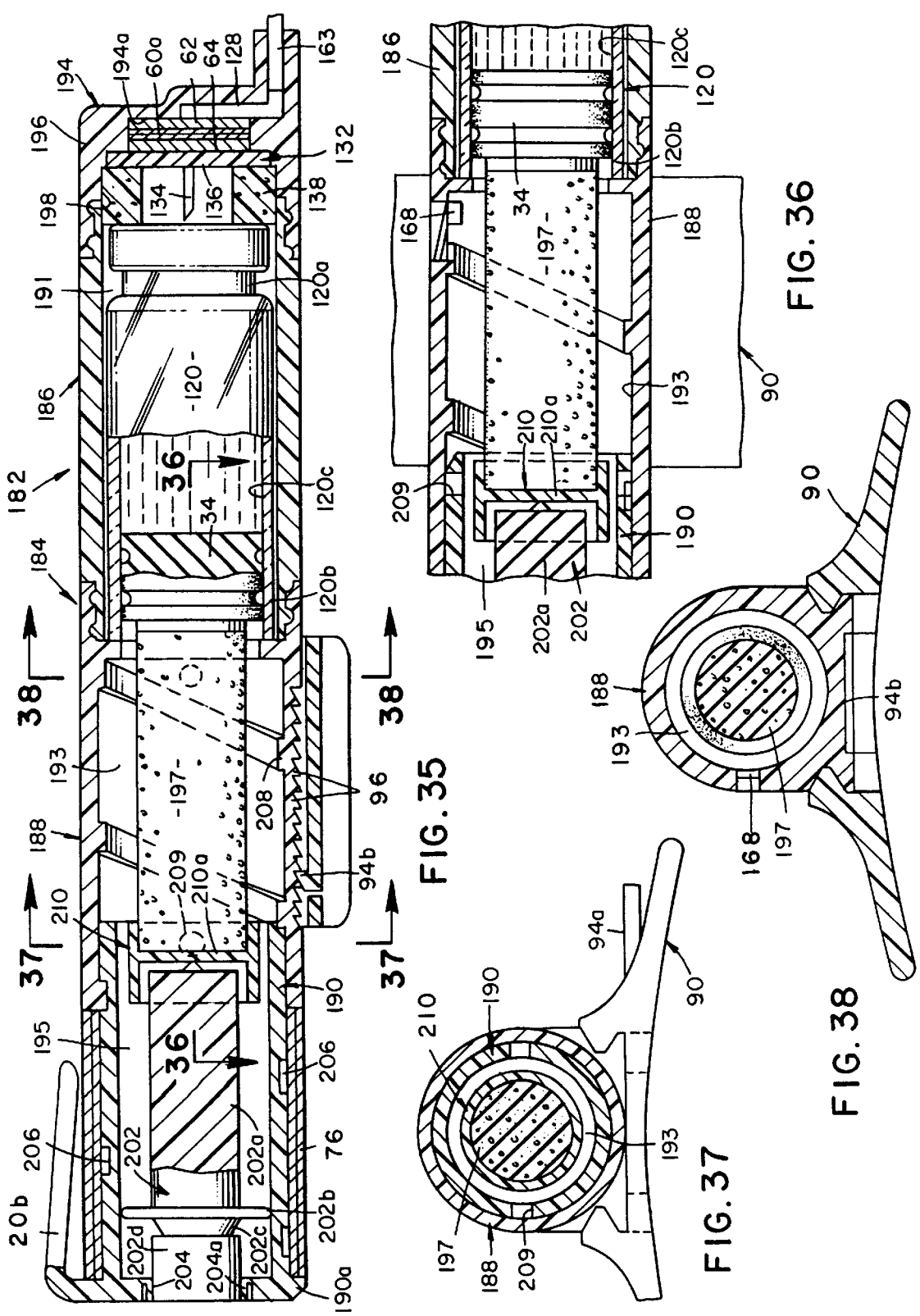

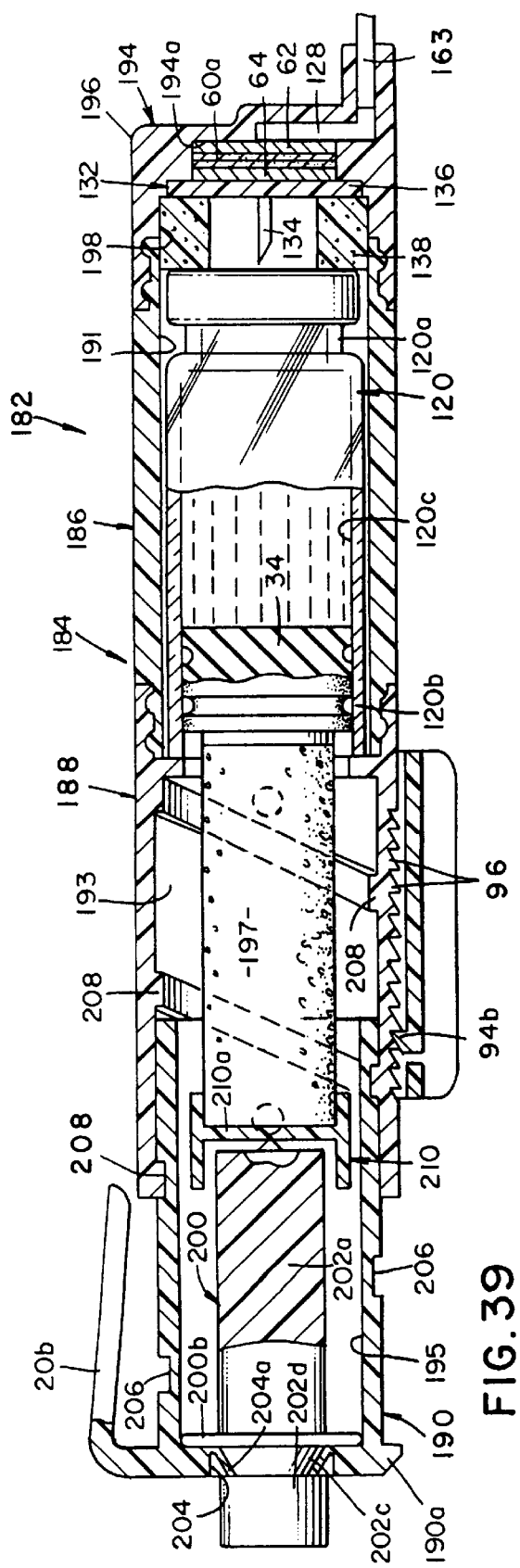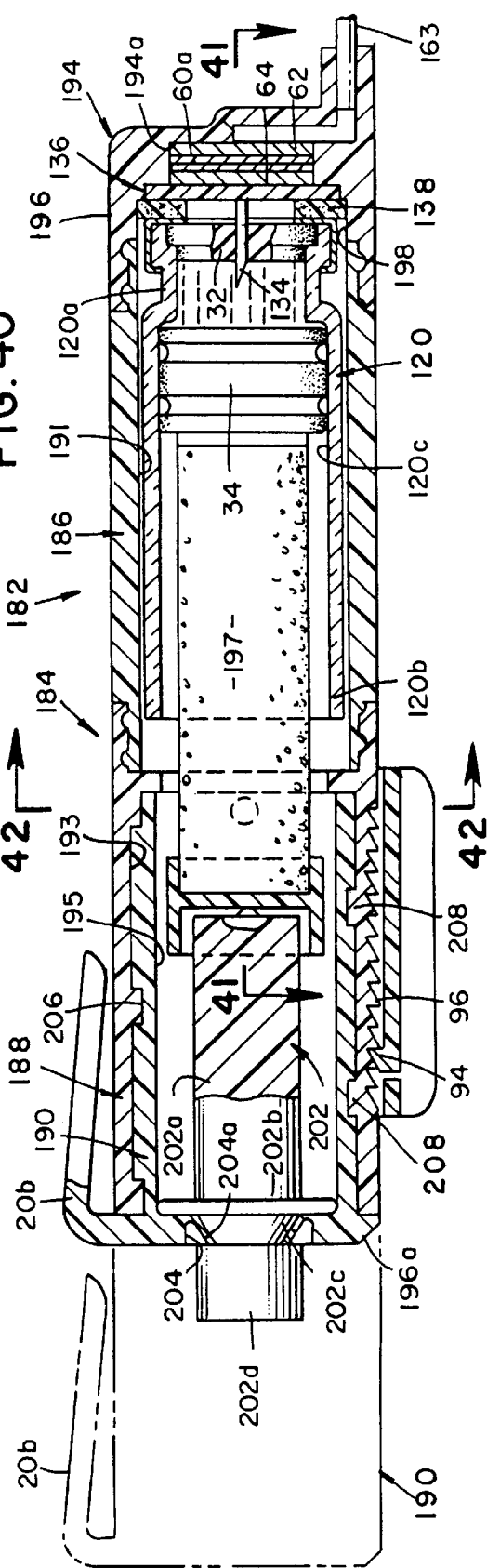

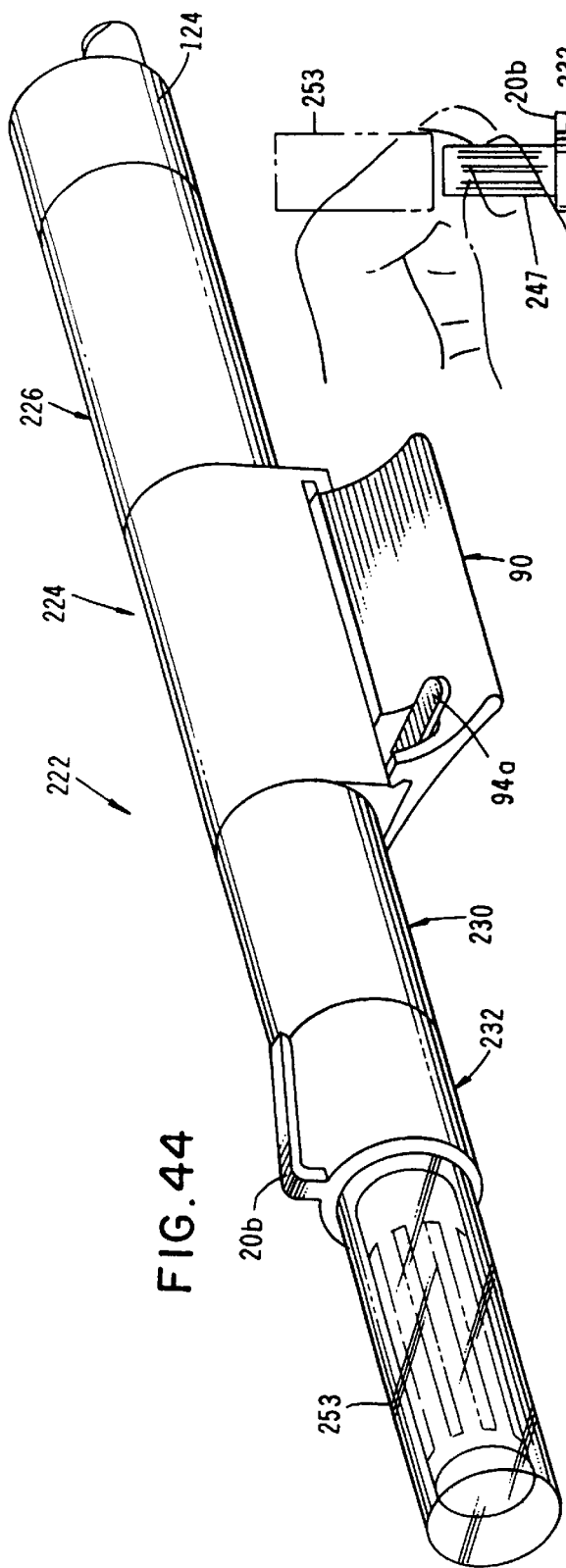
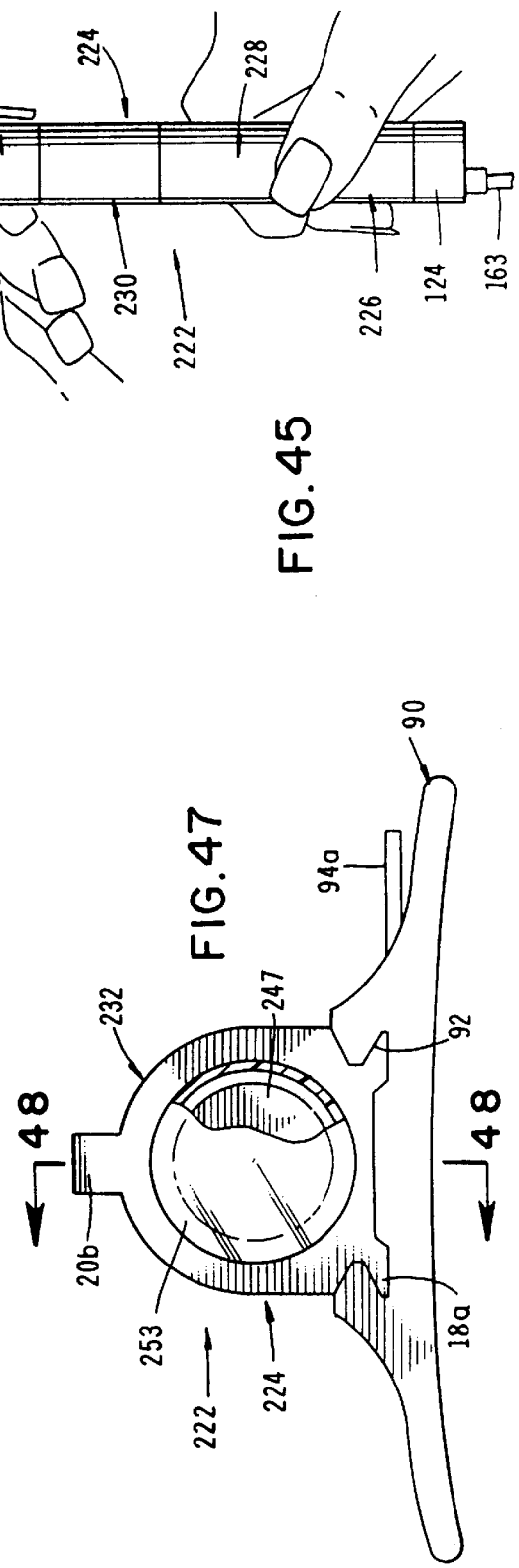

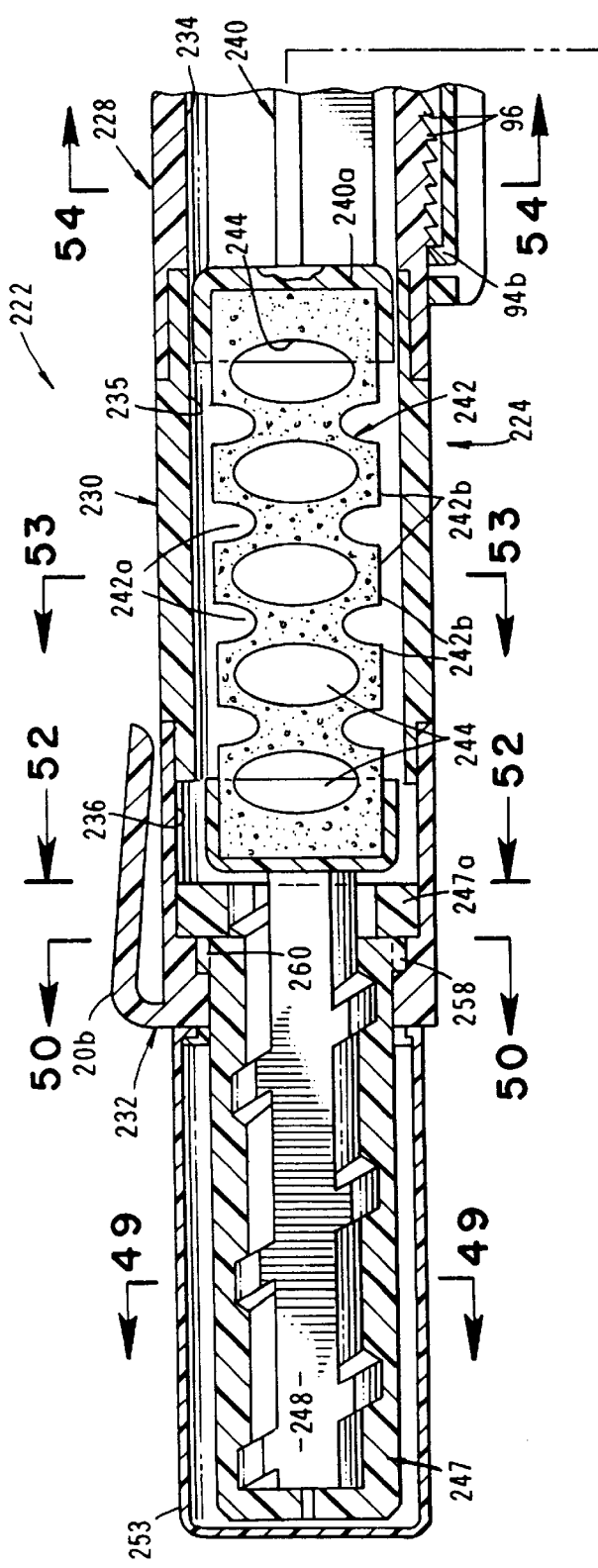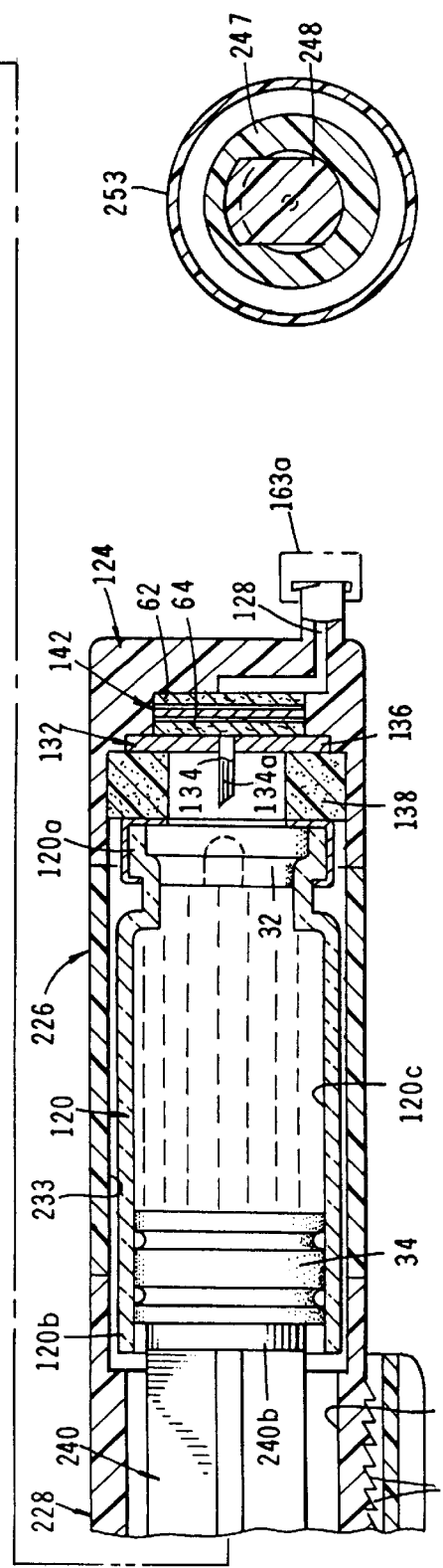
FIG. 49
FIG. 48

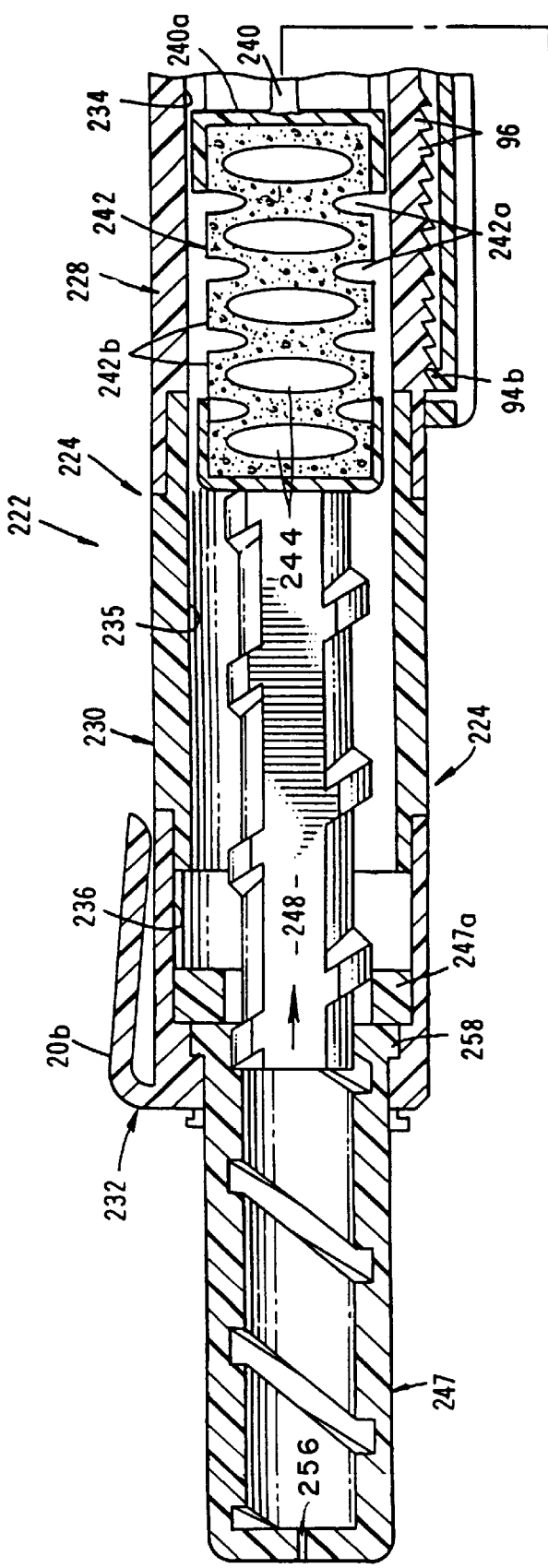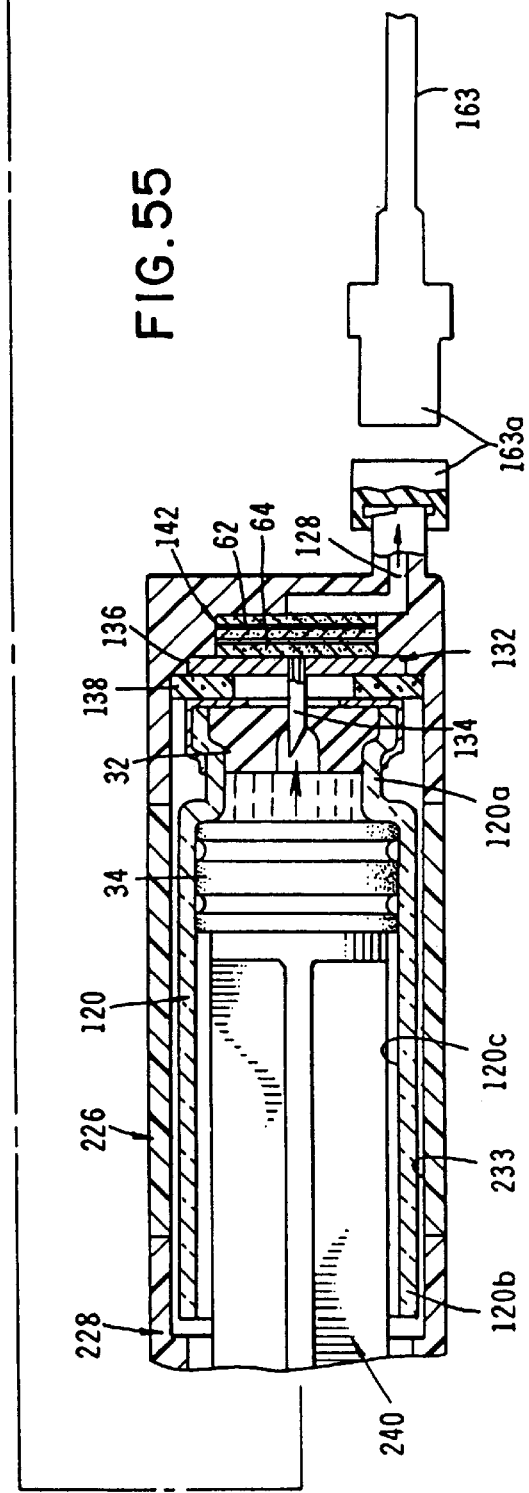
FIG. 55

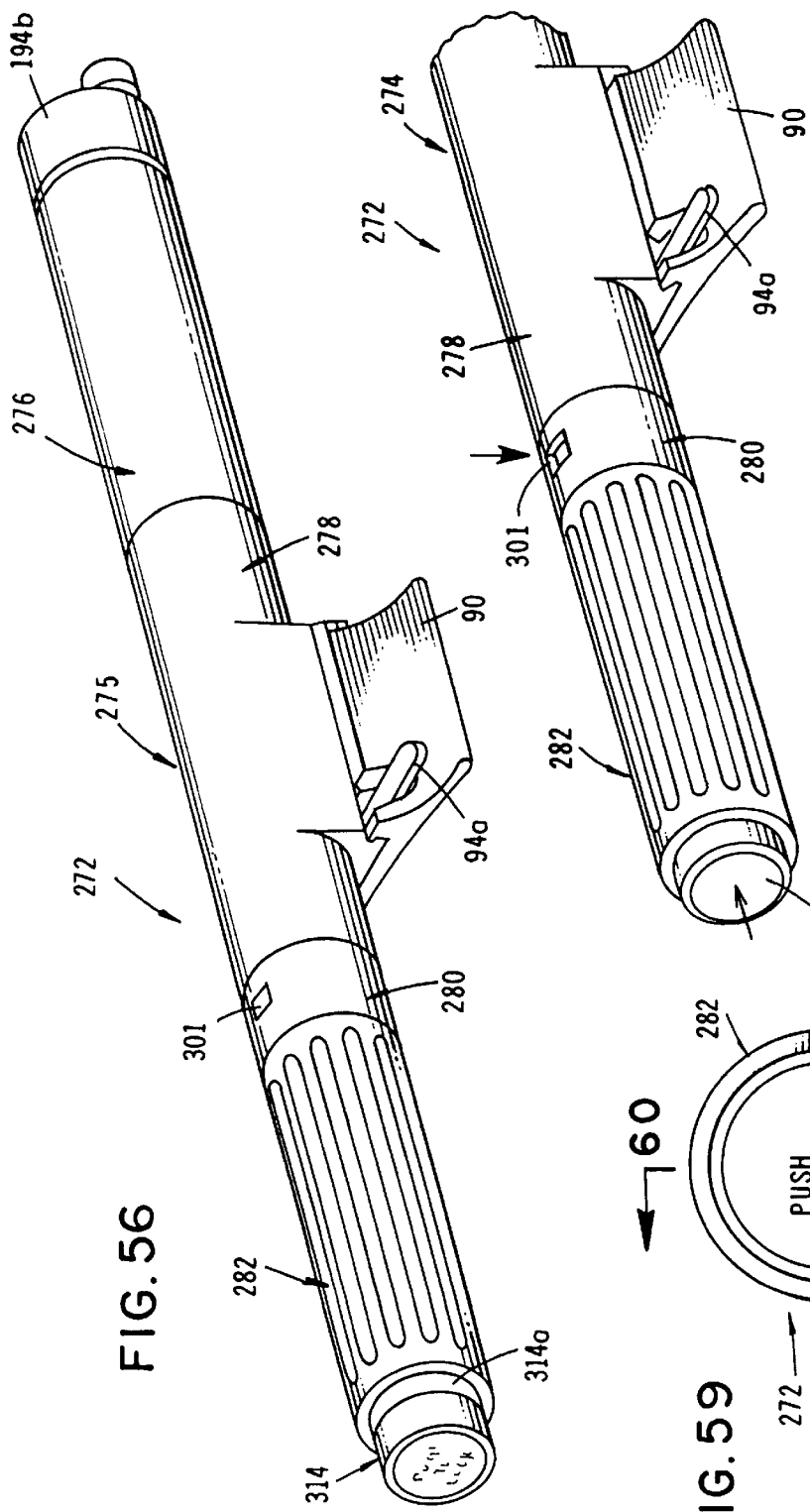
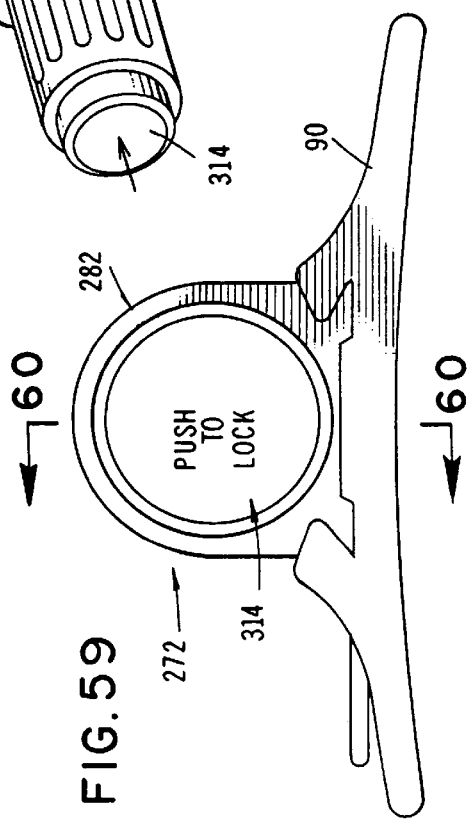

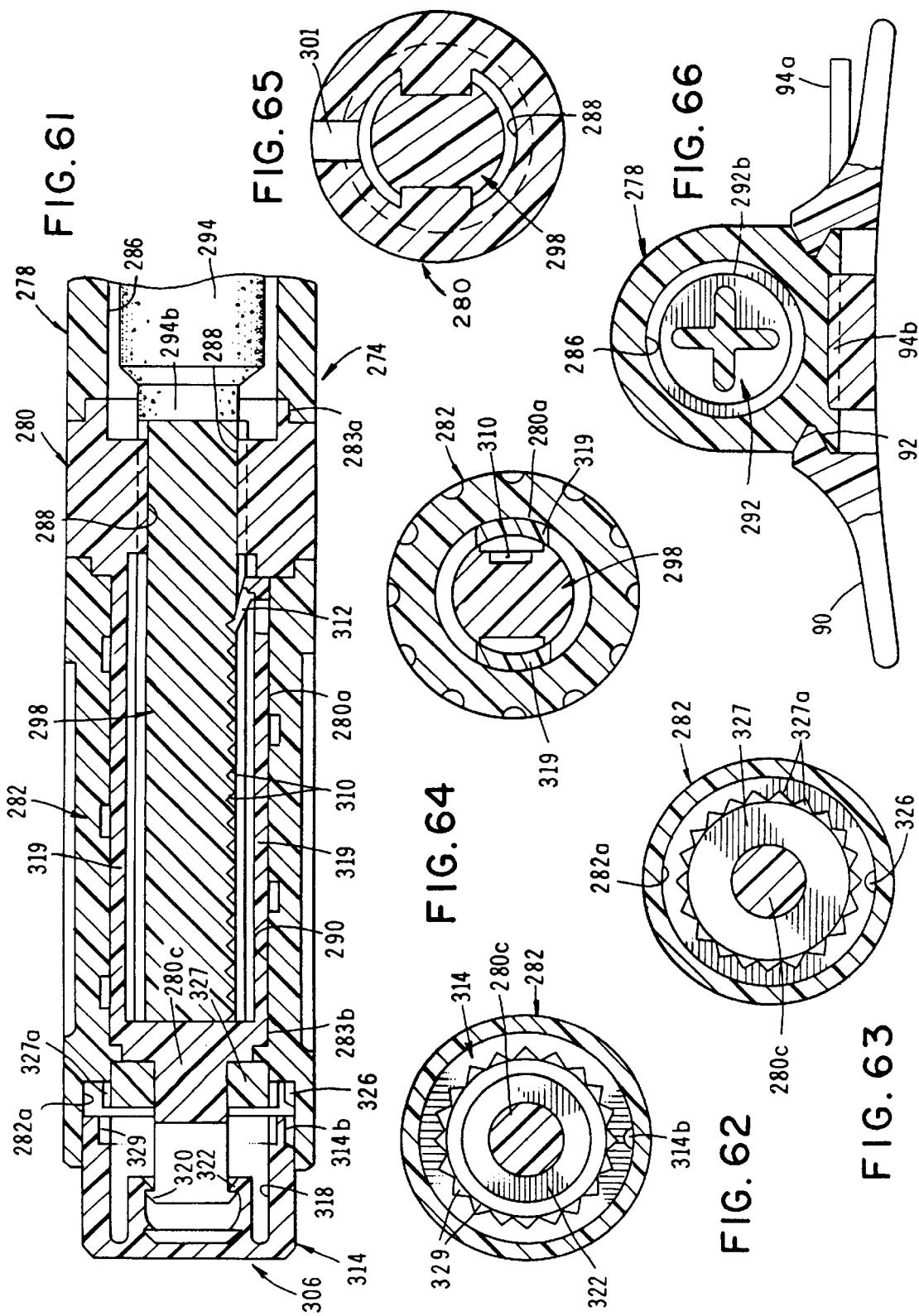

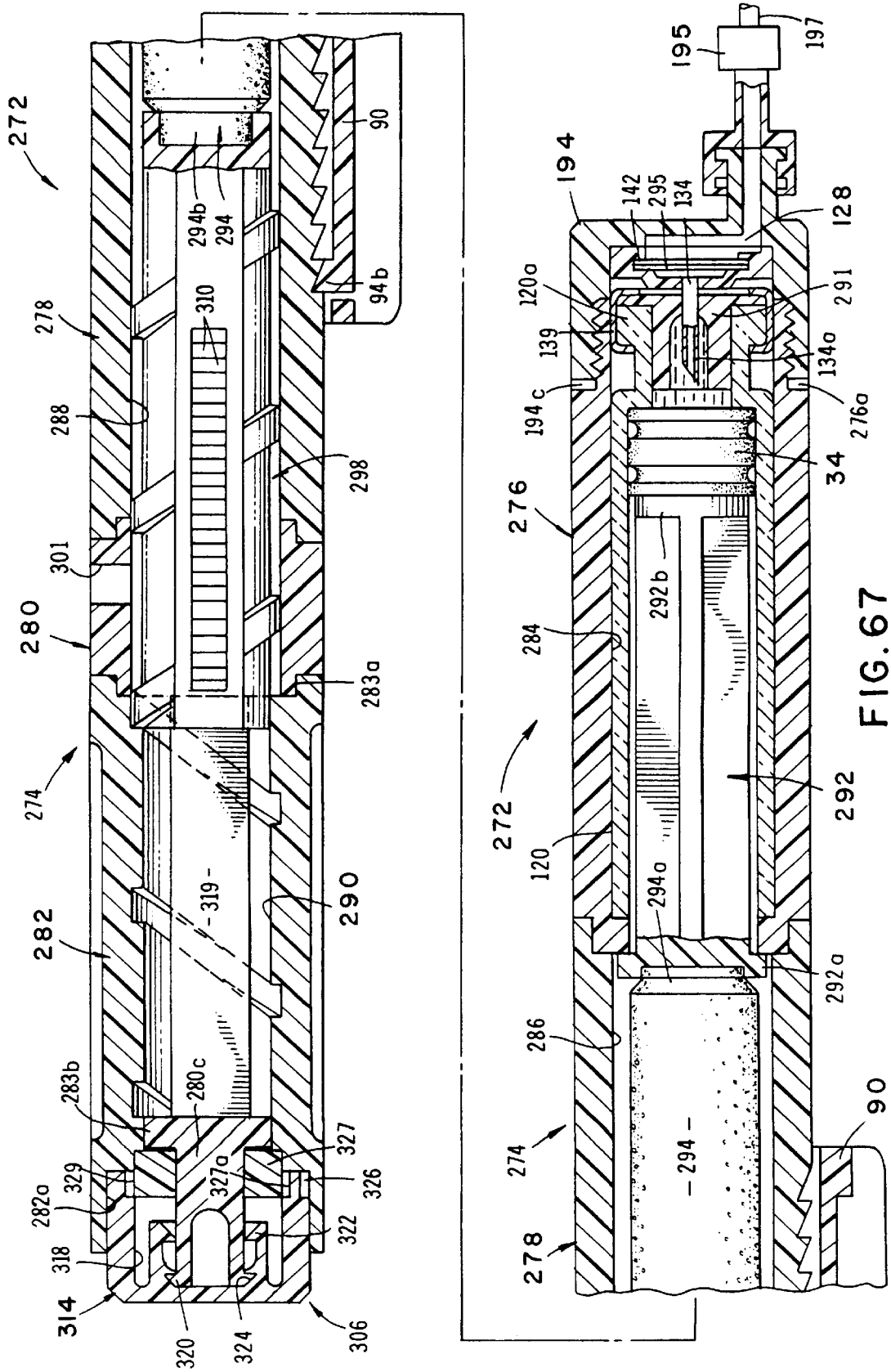

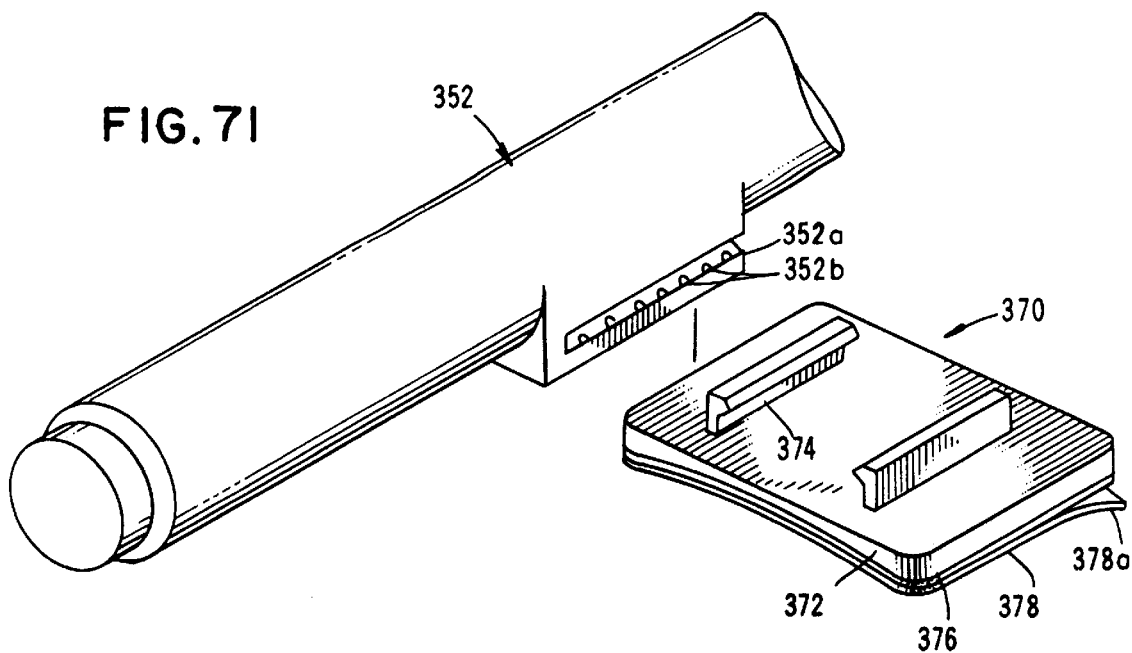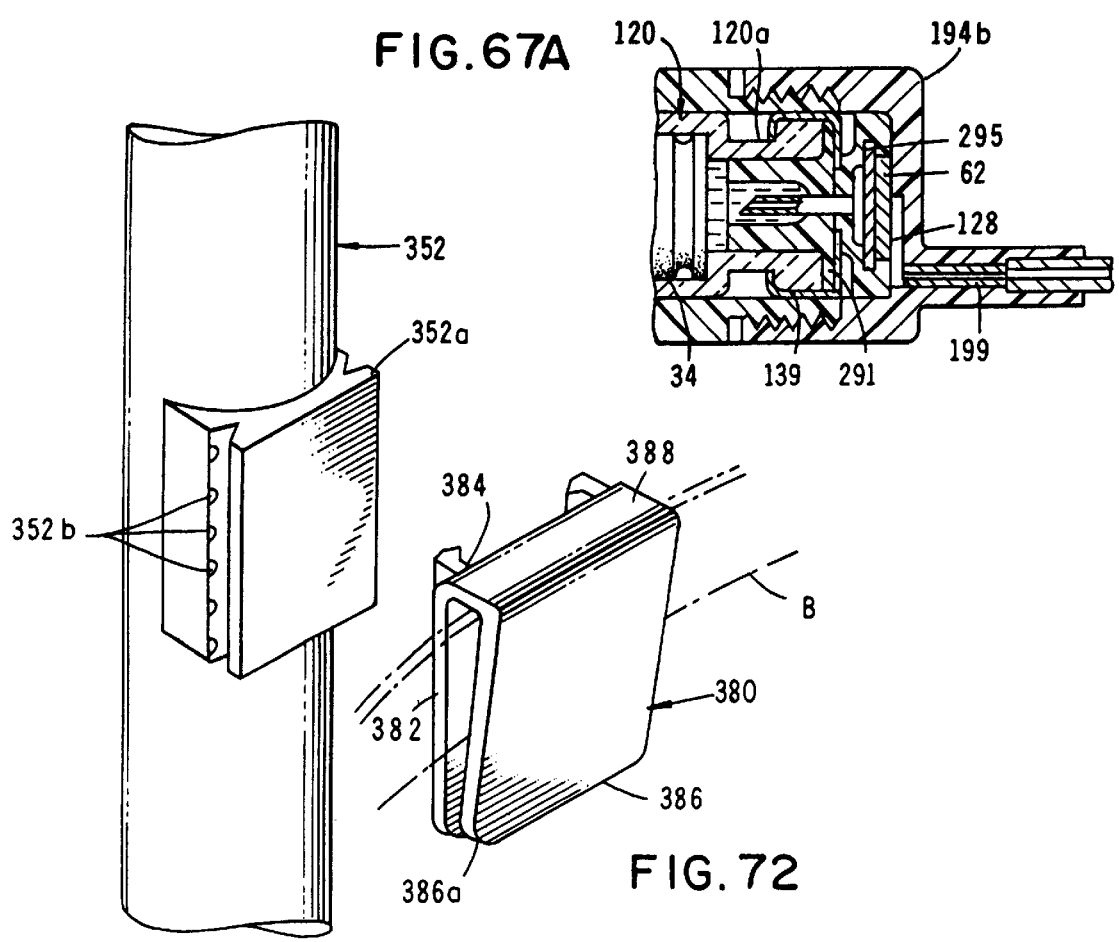

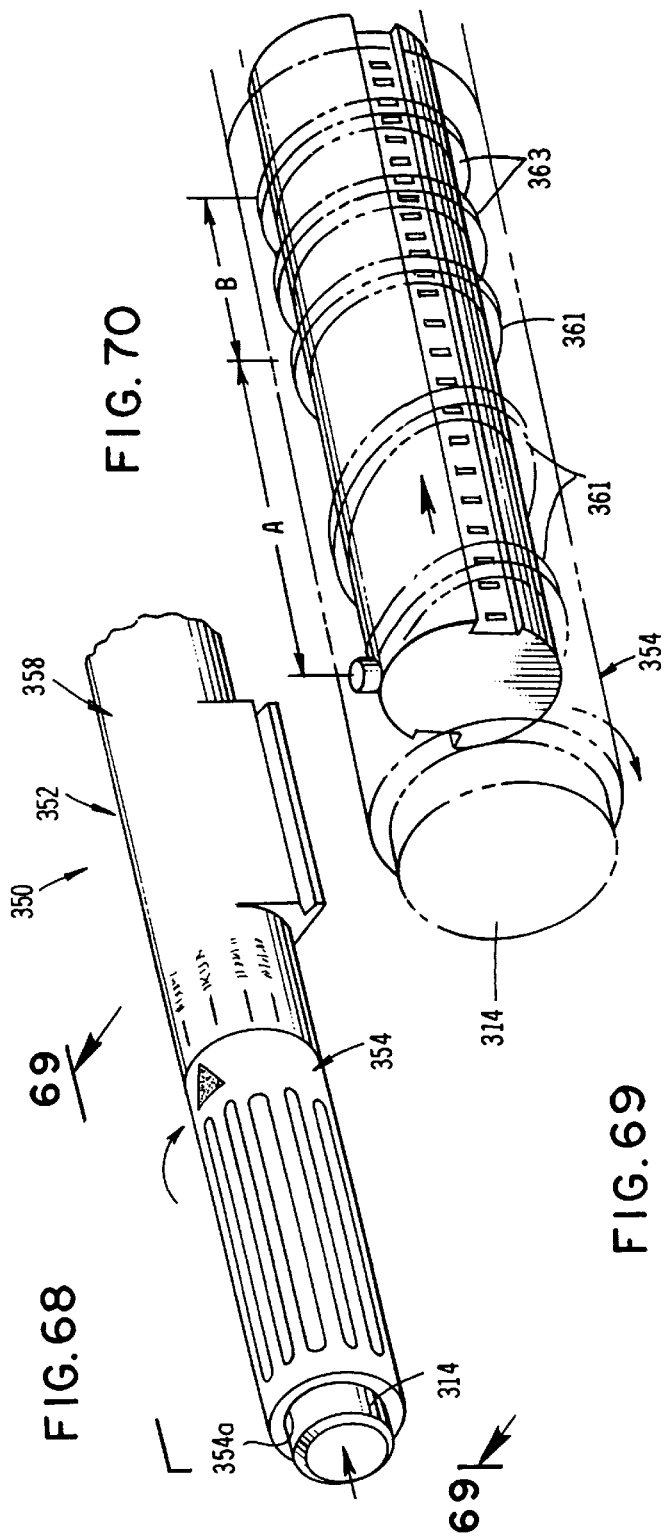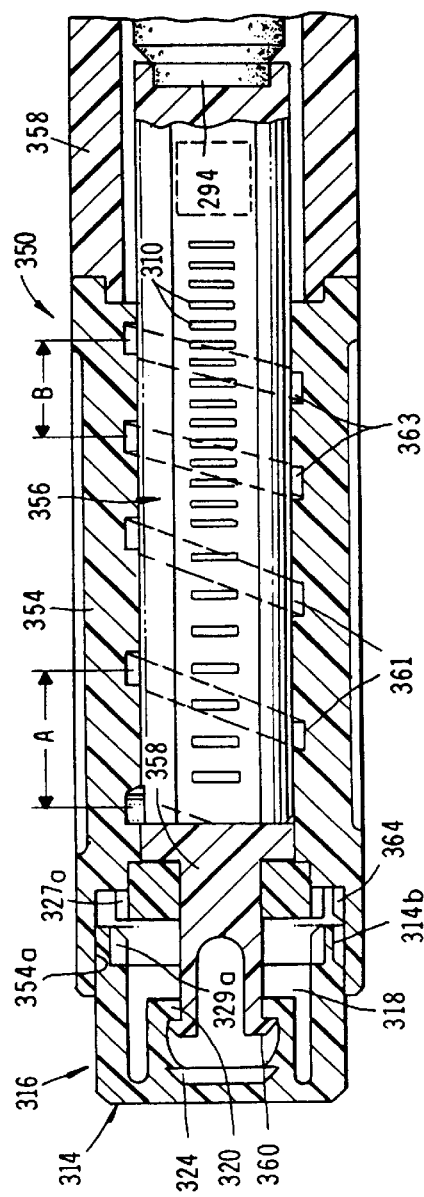

MEDICAMENT DISPENSER

This is a Continuation-In-Part of co-pending application Ser. No. 08/473,650 filed Jun. 6, 1995 which is a Continuation-In-Part of U.S. Ser. No. 08/349,496 filed Dec. 2, 1994.

BACKGROUND OF THE INVENTION

Field of the Invention

The present invention relates generally to fluid medicament dispensers. More particularly, the invention concerns a dispenser for use in controllably dispensing a liquid medicament as, for example, an insulin solution.

DISCUSSION OF THE INVENTION

Traditionally, conventional syringes are used to inject many beneficial agent solutions such as insulin. In accordance with conventional procedures, the prescribed dose is first drawn into the syringe and a visual check is made to make certain that the correct amount of insulin is present in the syringe. Next, air is expelled from the syringe and the dose is injected manually.

These conventional procedures have numerous drawbacks including adverse reaction caused by the bolus injection of drugs by hand via a syringe. In the majority of cases, the adverse reactions are not due to the drug itself, but rather are due to an improper rate of injection of the drug. Ideally, the contents of a syringe should be delivered over a number of minutes or hours. However, in clinical practice, this rarely occurs due to time pressure on the staff who must operate the syringe manually.

Because diabetics generally require regular and repeated injections of insulin, the use of self-delivering devices, such as conventional syringes, is cumbersome, time consuming, and dangerous if not properly performed. In addition, the process of sticking one's self and expulsing the liquid medicament can be extremely unpleasant for the medically untrained. For this reason, several types of dispensing devices have been suggested for automatically dispensing a predetermined quantity of a liquid medicament such as insulin from a multi-does container. Exemplary of such devices are those described in European Patent Application No. 37696 and in U.S. Pat. No. 4,592,745 issued to Rex, et al. Both of the aforementioned devices dispense a predetermined quantity of liquid from a liquid reservoir or container and both include mechanical operating mechanisms for expelling the fluid from the reservoir.

The Rex, et al device comprises an elongated body formed from two separable sections one of which contains an operating mechanism and the other of which contains a prefilled cartridge. The operating mechanism of the device mechanically advances an axially movable piston rod which, in turn, drives a piston plug located inside the cartridge so as to expel fluid from the device via a needle located at the bottom end of the body. The piston rod advances in successive axial steps of fixed length through rotation of a rotatable piston rod nut. The piston rod nut is driven by a rotatable worm, which is rotated by the advancing axial movement of a pressure device located at the top of the elongated body.

The EPO application discloses a dispensing device somewhat similar to the Rex, et al. device, but embodies an operating mechanism that comprises a pawl which permits relative movement of a ratchet-toothed member in a substantially rectilinear arrangement. As in the Rex, et al. device, the operating mechanism drives the plunger of a medicament vial to expel fluid therefrom.

U.S. Pat. No. 4,813,937 issued to Vaillancourt discloses an infusion system in which the inflow of fluid into the device causes an elastomeric member attached to a piston to be moved so as to stretch the elastomeric member. The thusly tensioned elastomeric member provides the source of energy to expel the fluid from the device when the outlet tubing of the system is opened. However, as is clear from a study of the Vaillancourt patent, the device disclosed therein operates in a substantially different manner than the device of the present invention.

Electrically operated syringe pumps are also well known, however, they are typically of considerable complexity and are designed to inject very small doses of medicine with considerable accuracy over a long period, which may be up to 24 hours. Such syringe pumps do not provide the inexpensive, simple and manually operated device suitable for the slow injection of drugs over a shorter period of time, which may range from one to 15 minutes.

Many of the prior art medicament dispensing devices are of complex construction and, therefore, are often very expensive to manufacture. Additionally, such devices tend to be somewhat unreliable in use and frequently have a limited useful life. In using certain of the prior art devices, maintaining sterility has also proven to be a problem.

As will be appreciated from the discussion which follows, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a constant-force spring that provides the force necessary to uniformly and precisely dispense solutions, such as insulin, from standard prefilled containers that can be conveniently loaded into the apparatus. Because of the simplicity of construction of the apparatus of the invention, and the straightforward nature of the energy source, the apparatus can be manufactured at low cost without in any way sacrificing accuracy and reliability.

SUMMARY OF THE INVENTION

It is an object of the present invention to provide a fluid dispenser for use in controllably dispensing fluid medicaments, such as insulin, antibiotics, oncolytics and the like from a prefilled container at a uniform rate.

Another object of the invention is to provide a dispenser of the aforementioned character in which a stored energy source is provided in the form of a highly novel, expandable, elastomeric member that provides the force necessary to continuously and uniformly expel fluid from the prefilled container.

Another object of the invention is to provide a dispenser of the character described in the preceding paragraph in which the expandable elastomeric member comprises a polymeric mass which can be controllably deformed and, after being deformed, exhibits a tendency to predictably return toward a non-deformed configuration.

Another object of the invention is to provide a dispenser of the class described which includes a fluid flow control assembly that filters and precisely controls the flow of the medicament solution from the prefilled container.

Another object of the invention is to provide a fluid dispenser which is adapted to be used with conventional prefilled insulin drug vials to deliver an insulin solution therefrom in a precise and sterile manner.

Another object of the invention is to provide a fluid dispenser of the class described which is compact, light weight, is easy for ambulatory patients to use, is fully disposable, and is extremely accurate so as to enable the infusion of precise doses of insulin over prescribed periods of time.

Another object of the invention is to provide a self-contained medicament dispenser which is of very simple construction and yet extremely reliable in use.

Another object of the invention is to provide a dispenser of the class described which includes means for interconnecting the device with the body or clothing of the patient.

Another object of the invention is to provide a fluid dispenser as described in the preceding paragraphs which is easy and inexpensive to manufacture in large quantities.

BRIEF DESCRIPTION OF THE DRAWINGS

FIG. 1 is a generally perspective view of one embodiment of the dispensing apparatus of the present invention for dispensing fluids at a uniform rate.

FIG. 2 is a generally perspective view showing the appearance of the apparatus of FIG. 1 after a portion of the operating member has been threadably advanced into the body portion of the apparatus.

FIG. 2A is a generally perspective, diagrammatic view illustrating the manner in which a portion of the operating member is advanced by the user into the body of the apparatus.

FIG. 3 is an enlarged right end view of the apparatus shown in FIGS. 1 and 2.

FIG. 4 is a generally perspective, exploded view of the apparatus of FIG. 1.

FIG. 5 is a generally perspective, exploded view of the fluid flow control assembly of the apparatus which functions to control the rate of fluid flow from the apparatus.

FIG. 7 is a cross-sectional view taken along lines 7—7 of FIG. 6.

FIG. 8 is a cross-sectional view similar to FIG. 7, but illustrating the operation of the housing release mechanism of the base support assembly.

FIG. 9 is a cross-sectional view taken along lines 9—9 of FIG. 6.

FIG. 10 is a cross-sectional view taken along lines 10—10 of FIG. 6.

FIG. 13 is a development view taken along lines 13—13 of FIG. 11 illustrating the manner in which the locking teeth and locking tabs of the device cooperate to lock the operating member to the housing.

FIG. 14 is a generally perspective view of an alternate embodiment of the dispensing apparatus of the present invention for dispensing fluids at a uniform rate.

FIG. 15 is a generally perspective view showing the appearance of the apparatus of FIG. 14 after a portion of the operating member has been threadably advanced into the body portion of the apparatus.

FIG. 16 is a generally perspective, exploded view of the apparatus of FIG. 14.

FIG. 17 is a generally perspective, exploded view of the fluid flow control assembly of this latest form of the apparatus which functions to control the rate of fluid flow from the apparatus.

FIG. 18 is a generally perspective, diagrammatic view illustrating the manner in which a portion of the operating member is threadably advanced by the user into the body of the apparatus.

FIG. 19 is an enlarged left end view of the apparatus shown in FIGS. 14 and 15.

FIG. 20 is an enlarged, cross-sectional view taken along lines 20—20 of FIG. 19.

FIG. 21 is a cross-sectional view taken along lines 21—21 of FIG. 20.

FIG. 22 is a cross-sectional view taken along lines 22—22 of FIG. 20.

FIG. 23 is a cross-sectional view taken along lines 23—23 of FIG. 20.

FIG. 24 is an enlarged, cross-sectional view similar to FIG. 20, but showing the position of the component parts of the apparatus after a portion of the operating member has been threadably advanced into the body.

FIG. 25 is a cross-sectional view similar to FIG. 24 but illustrating the position of the cooperating component parts after the cannula has pierced the piercable septum of the medicament vial.

FIG. 29 is a generally perspective view of an alternate embodiment of the dispensing apparatus of the present invention for dispensing fluids at a uniform rate.

FIG. 30 is a generally perspective view showing the appearance of the apparatus of FIG. 29 after a portion of the operating member has been threadably advanced into the body portion of the apparatus.

FIG. 31 is a generally perspective, exploded view of the apparatus of FIG. 29.

FIG. 32 is a generally perspective, exploded view of the fluid flow control assembly of this next form of the apparatus which functions to control the rate of fluid flow from the apparatus.

FIG. 33 is a generally perspective, diagrammatic view illustrating the manner in which a portion of the operating member is advanced by the user into the body of the apparatus.

FIG. 34 is an enlarged left-end view of the apparatus shown in FIGS. 29 and 30.

FIG. 35 is an enlarged, cross-sectional view taken along lines 35—35 of FIG. 34.

FIG. 36 is a cross-sectional view taken along lines 36—36 of FIG. 35.

FIG. 37 is a cross-sectional view taken along lines 37—37 of FIG. 35.

FIG. 38 is a cross-sectional view taken along lines 38—38 of FIG. 35.

FIG. 39 is an enlarged, cross-sectional view similar to FIG. 35, but showing the position of the component parts of the apparatus after a portion of the operating member has been threadably advanced into the body.

FIG. 40 is a cross-sectional view similar to FIG. 39 but illustrating the position of the cooperating component parts after a portion of the operating member has been further advanced into the body and the cannula has pierced the piercable septum of the medicament vial.

FIG. 44 is a generally perspective view of yet another embodiment of the dispensing apparatus of the present invention for dispensing fluids at a uniform rate.

FIG. 45 is a generally perspective, diagrammatic view illustrating the manner in which the threaded compression cap is advanced by the user into the body of the apparatus.

FIG. 47 is an enlarged left end view of the apparatus shown in FIG. 44.

FIG. 48 is a cross-sectional view taken along lines 48—48 of FIG. 47.

FIG. 49 is a cross-sectional view taken along lines 49—49 of FIG. 48.

FIG. 55 is a cross-sectional view similar to FIG. 48, but showing the position of the component parts of the apparatus after the control rod of the device has been threadably advanced into the body.

FIG. 56 is a generally perspective view of still another embodiment of the dispensing apparatus of the present invention.

FIG. 57 is a generally perspective, fragmentary view illustrating the appearance of the device after the locking push button has been advanced by the user into the forward portion of the body of the apparatus.

FIG. 59 is an enlarged left end view of the apparatus shown in FIG. 56.

FIG. 61 is a cross-sectional view taken along lines 61—61 of FIG. 60.

FIG. 62 is a cross-sectional view taken along lines 62—62 of FIG. 60.

FIG. 63 is a cross-sectional view taken along lines 63—63 of FIG. 60.

FIG. 64 is a cross-sectional view taken along lines 64—64 of FIG. 60.

FIG. 65 is a cross-sectional view taken along lines 65—65 of FIG. 60.

FIG. 66 is a cross-sectional view taken along lines 66—66 of FIG. 60.

FIG. 67 is a cross-sectional view similar to FIG. 60 but showing the position of the components of the device following the dispensing of the fluid from the fluid reservoir.

FIG. 67A is a fragmentary cross-sectional view of an alternate form of the flow control assembly of the invention shown in FIG. 67.

FIG. 68 is a generally perspective, fragmentary view of yet another embodiment of the dispensing apparatus of the present invention.

FIG. 69 is an enlarged cross-sectional view taken along lines 69—69 of FIG. 68.

FIG. 70 is a generally perspective, diagrammatic view illustrating the special threaded configuration of the operating means of this latest form of the invention.

FIG. 71 is a generally perspective, exploded view of another form of supporting base of the dispensing apparatus of the invention.

FIG. 72 is a generally perspective, exploded view of still another form of the supporting base, shown here as comprising a belt clip.

DESCRIPTION OF THE INVENTION

Figure 6:
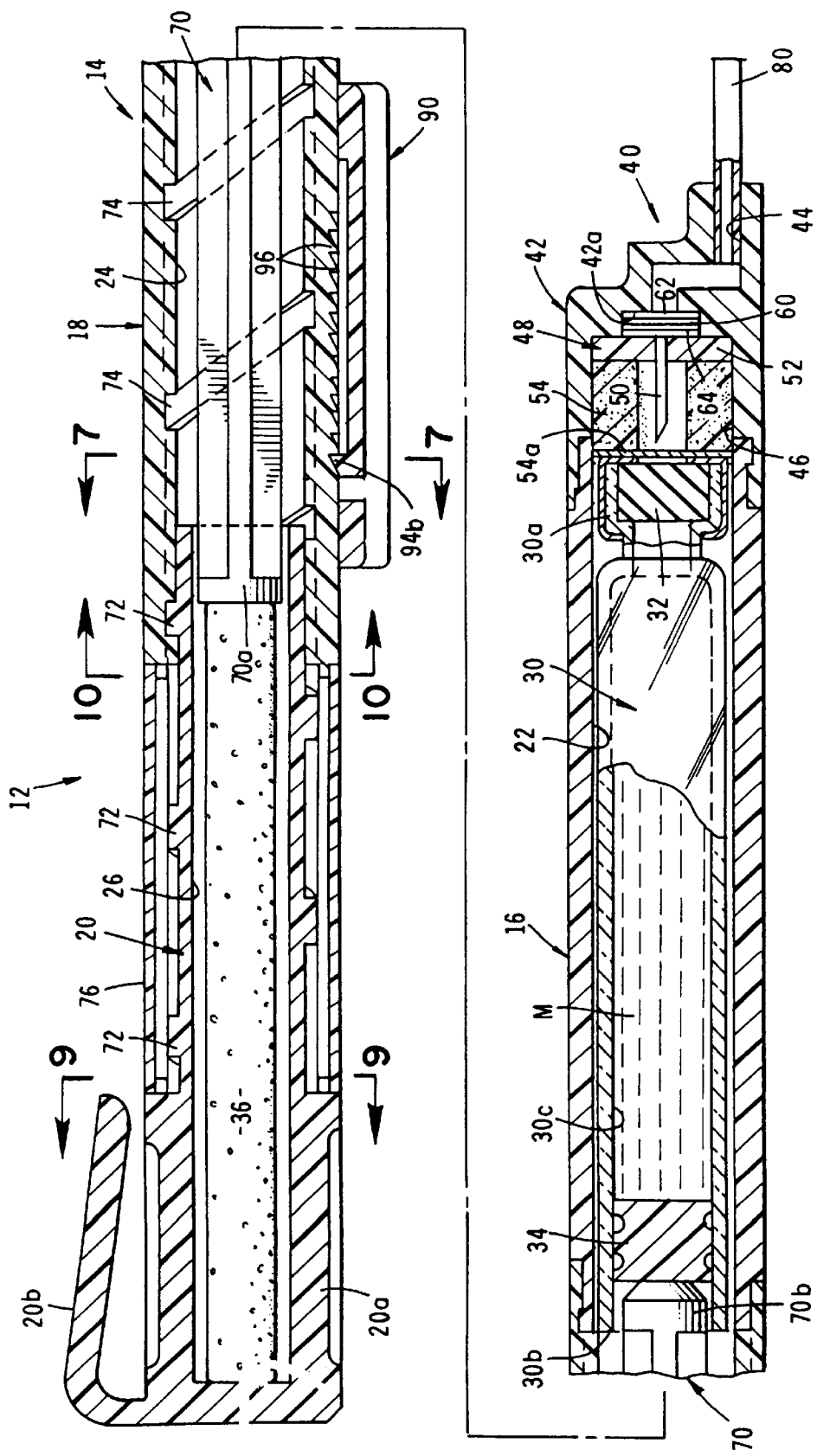
FIG. 6 is an enlarged, cross-sectional view taken along lines 6—6 of FIG. 3.

Referring to the drawings and particularly to FIGS. 1 through 5, one embodiment of the dispensing apparatus of the present invention is there illustrated and generally designated by the numeral 12. The apparatus of this form of the invention comprises an elongated body 14, which is made up of three interconnected, generally tubular shaped portions 16, 18, and 20 respectively, portion 20 comprising the operating means of the invention, the purpose of which will presently be described. As best seen by referring to FIG. 6, when portions 16, 18, and 20 are interconnected to form elongated body 14, they define first, second and third communicating interior chambers 22, 24, and 26 respectively.

Removably receivable within first chamber 22 is a prefilled medicament vial 30 having a first end 30a sealed by a piercable member 32 and a second end 30b sealed by an elastomeric plunger 34 which is telescopically movable longitudinally of the internal fluid reservoir or chamber 30c of vial 30. Pierceable member 32 comprises a part of the outlet means of the reservoir for permitting fluid flow therefrom.

Disposed within second chamber 24 of elongated body 14 is plunger engaging means for moving plunger 34 of the vial assembly axially of chamber 30c. The details of construction and operation of this plunger engaging means and its interrelationship with the operating means will presently be described. Disposed within third chamber 26 of the elongated body is the highly novel and important stored energy means of the invention, which provides energy necessary to move plunger 34 longitudinally of reservoir 30c. This unique stored energy means here comprises a compressively deformable elastomeric, polymeric mass 36 which is movable from a first configuration shown in FIG. 6 to a second, more compressed configuration wherein it has a tendency to return toward its first expanded configuration. The method and apparatus for controllably compressively deforming elastomeric member 36, which includes operating member 20 and its finger-engaging portion 20a (FIG. 1), will be described in the paragraphs which follow.

Also comprising an important aspect of the apparatus of the present form of the invention is flow control means for controlling the outward flow of fluid flowing from the reservoir or internal chamber 30c of vial 30. This flow control means here comprises a body portion provided in the form of an end cap assembly 40 which is threadably interconnectable with body portion 16. As best seen by referring to FIGS. 5 and 6, cap assembly 40 comprises an internally threaded cap 42 having a fluid outlet 44 and defining an interior chamber 46. Disposed within chamber 46 and forming a part of the flow control means of the invention is a cannula assembly 48 which comprises a hollow cannula 50 and a cannula support plate 52. Cannula 50 can be either a conventional, sharp, hollow needle or a blunt end cannula of a character well known in the art. Cannula assembly 48 is held in position within cap 42 by sonic bonding or the like. Disposed adjacent plate 52 is a spacer means, shown here as a compressible, elastomeric spacer plug assembly 54, which includes a pierceable membrane 54a that is receivable within the mouth of cap chamber 46 in the manner shown in FIG. 6. Prior to the cap assembly being interconnected with body portion 16 interior chamber 46 of the cap assembly is closed and maintained in a sterile configuration by a tearaway cap 58 (FIG. 5).

Disposed between cannula support plate 52 and an end wall 42a of cap 42 (FIG. 6) is rate control means for controlling the rate of fluid flowing outwardly through outlet 44 of cap 42. This fluid rate control means comprises a part of the fluid flow control means of the invention and, in the form of the invention shown in the drawings, includes a rate control membrane 60. Rate control membrane 60, which can be constructed from any suitable porous material such as a polycarbonate, a metal or a ceramic, is disposed between two fluid distribution plates 62 and 64. These distribution plates, which comprise a part of the fluid distribution means of the invention, function to uniformly distribute fluid flowing through cannula 50 in radially outwardly directions so that the fluid will uniformly flow through the face of the rate control membrane 60. Distribution plate 62 functions as a substrate support for membrane 60 and also functions to redistribute and manifold the fluid and direct its flow uniformly inwardly toward outlet 44 of cap assembly 42. Distribution plates 62 and 64 can be constructed of any suitable porous material of a character well known by those skilled in the art as by way of example, porous polypropylene, porous polycarbonate, and porous polysulfone.

In using the apparatus of the invention shown in FIGS. 1 through 13, the component parts of the apparatus are assembled in the manner shown in FIG. 6. More particularly, fluid vial 30 containing a fluid such as the medicament "M", which may be insulin, antibiotics, oncolytics, human growth hormones, or any other type of injectable beneficial agent, is inserted into first chamber 22 of the elongated body. End assembly 42 is then threadably interconnected with body portion 16. Next, the plunger engaging means shown here as an elongated pusher member 70 is inserted into second chamber 24 in the manner shown in FIG. 6. This done, the stored energy means, or elastomeric member 36, is inserted into chamber 26 of the third, or operating member, portion of elongated body 14. It is to be noted that body 20 of the operating member is provided with threads 72 (FIG. 4) which engage internal threads 74 that are formed internally of second body portion 18. Prior to use of the device, member 20 is connected to, but not fully threaded into body portion 18. When initially connected, the operating member extends outwardly from body portion 18 in the manner shown in FIG. 1. To protect threads 72 and to prevent accidental loading of the stored energy means, a scored plastic, tubular tearaway covering 76 surrounds body portion 20 in the manner shown in FIGS. 1 and 6.

Figure 11:
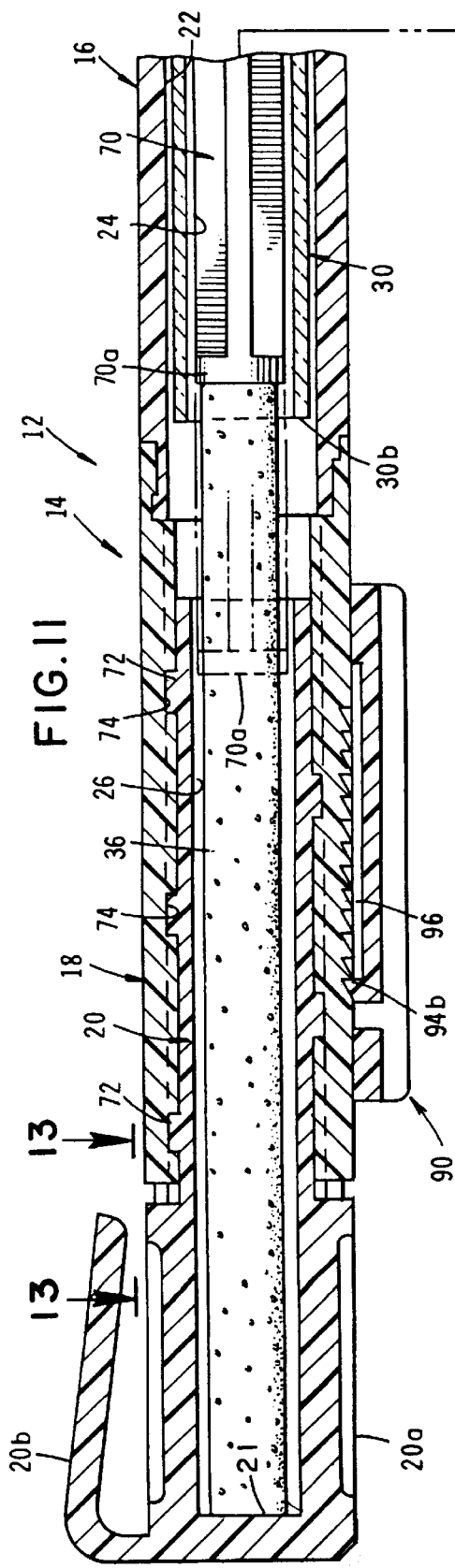
FIG. 11 is an enlarged, cross-sectional view similar to FIG. 6, but showing the position of the component parts of the apparatus after a portion of the operating member has been threadably advanced into the body.
Figure 12:
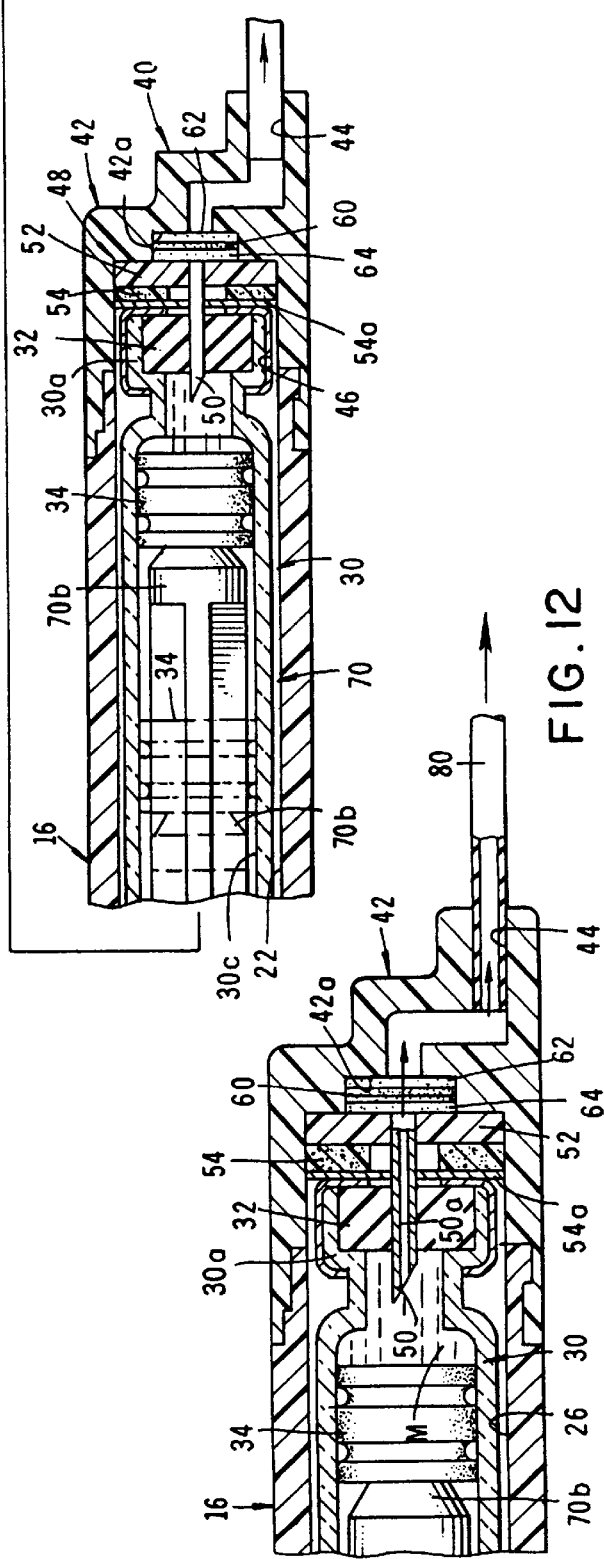
FIG. 12 is a fragmentary, cross-sectional view of the dispensing end portion of the apparatus illustrating the position of the cooperating component parts after the cannula has pierced the piercable septum of the medicament vial.
Figure 26:
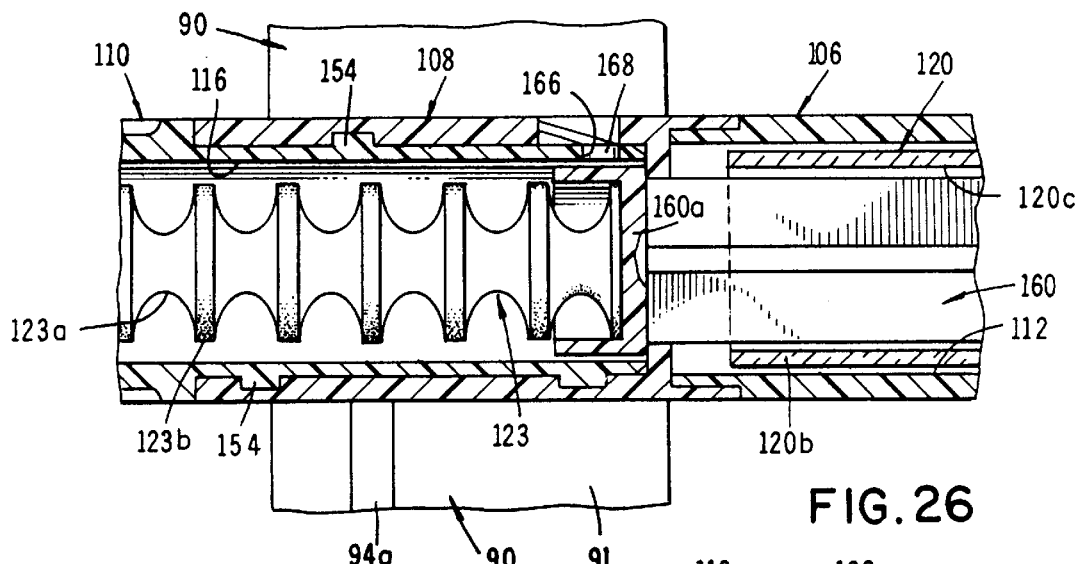
FIG. 26 is a cross-sectional view taken along lines 26—26 of FIG. 25.
Figure 27:
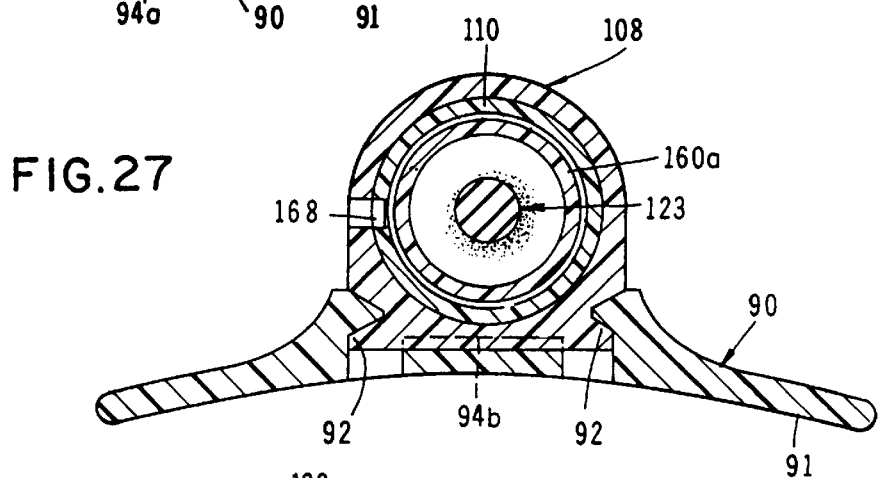
FIG. 27 is a cross-sectional view taken along lines 27—27 of FIG. 25.

After the apparatus has been assembled in the manner shown in FIGS. 1 and 6, and prior to its being used, covering 76 is pealed away from body portion 20 in the manner depicted in FIG. 1. This done member 20 is threadably advanced inwardly of body portion 18 using finger-engaging portion 20a in the manner illustrated in FIGS. 2 and 2A. Turning to FIG. 11, it is to be noted that, as operating member 20 is threaded into body portion 18, the head portion 70a of pusher member 70 will engage and progressively deform elastomeric member 36 between member 70 and the internal end wall 21 of member 20 in the manner indicated by the phantom lines of FIG. 11. It is to be understood that member 36 can be deformed at a uniform rate or it can be deformed at a non-uniform rate depending upon the material used to construct the stored energy means and the specific end application to be made of the apparatus. As member 36 is strategically compressively deformed, the opposite end 70b of pusher member 70 will forcefully engage plunger 34 of the vial assembly tending to urge the plunger inwardly of the fluid reservoir in the manner shown in FIG. 6. It is to be noted that upon initial assembly of the apparatus spacer means, or spacer 54, maintains separation between cannula 50 and septum 32. However, because of the resistance offered by the fluid within the vial reservoir to axial movement of plunger 34, the entire vial assembly 30 will be moved to the right as viewed in FIG. 6 causing the compression of elastomeric spacer 54 and simultaneously causing cannula 50 to pierce piercable member 32 of the medicament vial assembly in the manner best illustrated in FIG. 12. As the cannula pierces the septum, or member 32, a fluid flow path will be opened between the medicament reservoir of the vial and the outlet port 44 of cap assembly 42 permitting the medicament to flow from the reservoir, through the flow control means of the invention and then outwardly of the apparatus through a conduit 80 which is connected to the outlet 44 of the cap assembly in the manner shown in FIG. 12. Conduit 80 is typically provided in the form of a microbore, flexible tubing which can be interconnected with a conventional infusion needle or a conventional infusion set (not shown). As seen in FIGS. 11 and 12, as the medicament vial moves to the right, elastomeric spacer plug 54, which previously maintained a spaced relationship between cannula 50 and piercable member 32, will be compressed from the expanded configuration shown in FIG. 6 to the compressed configuration shown in FIGS. 11 and 12.

After the fluid flow path between reservoir 30c and outlet 44 is open, the stored energy source, or elastomeric member 36 has a tendency to return toward its initial, less deformed starting configuration. In this regard, it is to be understood that, at the time of initial assembly of the device, member 36 can be either partially compressed, fully extended or strategically elongated. Expansion of compressed member 36 during the stored energy unloading phase causes plunger 34 to move axially of reservoir 30c from a first position shown in FIG. 6 to a second position shown in FIGS. 11 and 12. As the plunger moves within the reservoir, the fluid contained therein will be urged into a central fluid passageway 50a of cannula 50 and toward the flow control means of the apparatus. Fluid flowing from passageway 50a will controllably flow through rate control member 64, outwardly of outlet 44 and into conduit 80.

The various fluids that can be dispensed from vial 30, in addition to those previously described, include, by way of example, beneficial agents, such as medicaments of various types, drugs, pharmaceuticals, hormones, antibodies, biologically active materials, elements, chemical compounds or any other material useful in the diagnosis, cure, mitigation, treatment or prevention of disease, and for the maintenance of the good health of the patient.

With respect to the important stored energy means, a wide variety of materials can be used to form the stored energy means including rubbers, plastics and other thermoplastic elastomers (TPE) and thermoplastic urethane (TPU). By way of example, suitable materials include latex rubber, rubber polyolefins, polyisoprene (natural rubber), butyl rubber, nitrile rubber, polyurethane, vinyls, vinyl-endblocked polydimethylsiloxanes, other homopolymer, copolymers (random alternating, block, graft cross-link and star block), silicones and other flouropolymers, mechanical poly-blends, polymer alloys and interpenetrating polymer networks.

Examples of material found particularly well suited for constructing the stored energy means include porous and cellular systems including open and closed cell products such as highly resilient, flexible polyurethane foams, elastomeric silicone foams, latex rubber foam and other cellular rubber materials such as styrenebutadiene rubber (SBR).

Interpenetrating polymer networks (IPNS), which can also be used for the stored energy means, are unique blends of cross-linked polymers containing essentially no covalent bonds, or grafts between them. True IPNS are also homogeneous mixtures of component polymers.

The stored energy means can be constructed in a wide variety of shaped forms and configurations. It is to be noted that, particularly in latex rubber constructions, coring patterns in shaped form configurations significantly influence the compressive behavior of the cellular polymer.

Manufactures of materials suitable for use in the construction of stored energy source, include Advance Elastomer Systems, Dow Chemical, General Electric, B.P. Polymers, Mobay Chemical, Shell Oil Corp., Petrarch Systems, DuPont, Akron Rubber, Concept Polymers and Union Carbide Corp.

Referring now to FIGS. 9, 10 and 13, it is to be noted that housing portion 20 is provided with a plurality of circumferentially spaced teeth 84 while body portion 18 is provided with a plurality of circumferentially spaced, flexible, tab-like mating members 86. Teeth 84 along with tab-like members 86, comprise the locking means of this form of the invention for irreversibly interlocking the operating means or portion 20, with body portion 18 so as to effectively prevent accidental interruption of the unloading of the stored energy means. Referring particularly to FIG. 13, in which a segment of the locking means portion of the device shown in a linear portrayal, it can be seen that as member 20 moves into seating engagement with member 18, teeth 84 will yieldably deform flexible locking tabs 86 in the manner shown. Due to the sloping configuration of teeth 84, the locking tabs will readily pass over the teeth as the operating member is tightened, but then will spring outwardly against the vertical faces of the teeth so as to block rotation in an opposite direction thereby effectively preventing retraction of the operating member once it has been seated.

Turning next to FIGS. 1, 5, 7 and 8, the embodiment of the invention there shown comprises a support means for removably supporting body 14. This support means here includes a supporting base assembly 90, which is designed to be lockably interconnected with and securely support elongated body 14 in the manner shown in FIG. 2. As best seen in FIG. 3, base assembly 90 includes a curved base plate 91 which is provided with longitudinally extending channel 92 and a locking assembly 94 which includes a transversely extending, release arm 94a having a locking protuberance 94b (FIG. 4). Locking protuberance 94b is provided with a sloping face that is adapted to engage one of a plurality of outwardly extending locking ridges 96 provided on the base of body member 18 as flange portion 18a of member 18 is slidably received within groove 92 (FIG. 7).

With this construction, as flange 18a slides into groove 92 protuberance 94b will ratchet over teeth 96 until body portion 18 is finally seated within the base assembly. At this point (FIG. 11), tooth 96 will block removal of flange 18a (see also FIG. 7). However, upon depressing arm 94a in the manner shown in FIG. 8, protuberance 94b will pivot downwardly about leg 94c (FIG. 5) of the release mechanism so as to move clear of tooth 96 so that body portion 18 can be disengaged from the base assembly.

As will later be discussed, body 14 can be interconnected with other types of base assemblies which permit the interconnection therewith of a variety of fastening devices that enable the apparatus to be readily interconnected with the body or clothing of the ambulatory patient. These fastening devices are shown in FIGS. 71, 72, 73, and 74 and will be discussed hereinafter. When body 14 is disconnected from the base assembly, the body assembly can be conveniently carried in the users pocket with the pocket gripping finger 20b of finger-engaging portion 20a being used to frictionally engage the pocket.

Materials particularly well suited for the construction of the elongated body and the operating member include polycarbonates, nylons, and acrylics. Preferred materials for the construction of the pusher-engaging member include polypropylene, polystyrene and polyoxnyl chloride.

Referring now to FIGS. 14 through 28 of the drawings, an alternate form of the dispensing apparatus of the present invention is there illustrated and generally designated by numeral 102. The apparatus of this alternate form of the invention is similar in certain respects to the embodiment just described and like numbers have been used in FIGS. 14 through 18 to identify like components.

The apparatus of this alternate form of the invention comprises an elongated body 104, which is made up of three interconnected, generally tubular shaped portions 106, 108, and 110 respectively, portion 110 comprising a part of the operating means of this embodiment of the invention. As best seen by referring to FIG. 20, when portions 106, 108, and 110 are interconnected to form elongated body 104, they define first, second and third communicating interior chambers 112, 114, and 116 respectively.

As shown in FIG. 24, removably receivable within first chamber 112 is a prefilled medicament vial 120 of the general character previously described having a first end 120a sealed by a pierceable member 32 and a second end 120b sealed by an elastomeric plunger 34 which is telescopically movable longitudinally of the internal fluid reservoir of chamber 120c of vial 120. As before, pierceable member 32 comprises a part of the outlet means of the reservoir for permitting fluid flow therefrom.

Disposed within second chamber 114 of elongated body 108 is plunger engaging means for moving plunger 34 of the vial assembly axially of chamber 120c. The details of construction and operation of this plunger engaging means will presently be described.

Disposed within third chamber 116 of the elongated body is a slightly different form of the important stored energy means of the invention, which functions to operate the plunger engaging means. This unique stored energy means here comprises a specially configured elastomeric spring-like member 123 which is movable from a first configuration shown in FIG. 20 to a second, more compressed configuration wherein it has a tendency to return toward its first configuration. As best seen in FIG. 16, member 123 comprises an elongated member having a plurality of longitudinally spaced apart grooves and ridges 123a and 123b respectively.

The apparatus of this latest form of the invention also includes flow control means for controlling the outward flow of fluid flowing from the reservoir or internal chamber 120c of vial 120. The flow control means here comprises an end cap assembly 124 which is interconnectable with body portion 106 in any appropriate way, such as by adhesive, sonic, or radio frequency bonding. As best seen by referring to FIGS. 17 and 20, cap assembly 124 comprises a hollow cap 126 having a fluid outlet 128 (FIG. 20) and defining an interior chamber 130. Disposed within chamber 130 and forming a part of the flow control means of the invention is a cannula assembly 132 which comprises a hollow cannula 134 and a cannula support plate 136. As before, cannula 134 can be either a conventional, sharp, hollow piercing needle or a blunt end cannula mateable with a suitably configured septum 32 of a character well known in the art. Cannula assembly 132 is held in position within cap 126 by appropriate bonding. A compressible, elastomeric spacer plug 138, such as a low durometer silicone foam, is receivable within the mouth of cap chamber 130 in the manner shown in FIG. 20. Prior to the cap assembly being interconnected with body portion 106 interior chamber 130 of the cap assembly is closed and maintained in a sterile configuration by a tear-away cap 140 which is bonded to the cap (FIGS. 16 and 17).

Disposed between cannula support plate 132 and an end wall 126a (FIG. 20) of cap 126 is rate control means for controlling the rate of fluid flowing outwardly through outlet 128 of cap 126. This fluid rate control means comprises a part of the fluid flow control means of the invention and in this latest form of the invention includes a rate control assembly 142. Rate control assembly 142 comprises a laminate, which can be constructed from specially designed wafers 142a and 142b (FIG. 17), one of which comprises a filtering means or filter 145, for filtering particulates from the solution flowing from chamber 120c. The remaining wafers are constructed of porous material such as various polymers with alternate flow control pores of selected diameters and distribution patterns. Assembly 142 is supported by substrate 62 which functions as a distribution manifold for both the through flow and cross-flow of the fluid. The filter means can be constructed from a variety of materials including a porous polysulfone sold under the name and style "Supor" by Gilman Scientific of Detroit, Mich.

Turning particularly to FIGS. 15, 16, 20, and 24, it is to be noted that portion 110 of this latest form of the invention includes a unit condition indicator means for indicating that the apparatus has been placed into an operational condition. This indicator means here comprises an indicator element 146 which is carried within finger-engaging portion 110a of member 110. As seen in FIG. 25, element 146 includes a cylindrical body 146a, an enlarged diameter flange 146b, and a circumferentially extending groove 146c disposed proximate flange 146b. Body 146a is telescopically receivable within opening 148 provided in the end wall 111 of portion 110. Resiliently deformable locking tabs 150 are provided within opening 148 for locking engagement with groove 146c when the indicator is in the extended position shown in FIG. 25.

In using the apparatus of the invention shown in FIGS. 14 through 28, the component parts of the apparatus are assembled in the manner previously described and as shown in FIG. 20. As was the case with the earlier described embodiment, body 110 of the operating member is provided with threads 154 (FIG. 16) which engage internal threads 156 that are formed internally of second body portion 108 (FIG. 20). Prior to use of the device, member 110 is connected to, but not fully threaded into body portion 108. When initially connected the operating member extends outwardly from body portion 108 in the manner shown in FIGS. 14 and 20. As before, to protect threads 154, a covering 76 surrounds body portion 110 in the manner shown in FIGS. 14 and 20.

After the apparatus has been assembled in the manner shown in FIGS. 14 and 20, and prior to its being used, frangible covering 76 is pealed away from body portion 110 in the manner depicted in FIG. 14. This done, member 110 is threadably advanced inwardly of body portion 108 in the manner illustrated in FIGS. 15 and 18. Turning now to FIG. 24, it is to be noted that as the operating member 110 is threaded into body portion 108 using finger-grip portion 110a, the cup-shaped head portion 160a of a pusher member 160 will engage and progressively compress elastomeric member 123 either uniformly or non-linearly. Simultaneously the opposite end 160b of pusher member 160 will engage plunger 34 of the vial assembly in the manner shown in FIG. 24. As portion 110 moves toward a seated position, indicator element 146 will move from the retracted position shown in FIG. 20 to the extended position shown in FIG. 24. As the indicator element moves to its fully extended position, resiliently deformable tabs 150 will move into groove 146c so as to lock the indicator element in the fully extended position (see FIGS. 24 and 25). Indicator element 146 can be fabricated of a plastic material having a color different from that of member 110 and can carry indicia indicating that the device has been placed in a fluid condition. As before, because of the resistance offered by the fluid within the vial reservoir to axial movement of plunger 34, vial assembly 120 will be moved to the right as viewed in FIG. 24 causing the compression of elastomeric spacer 138 and simultaneously causing cannula 134 to pierce piercable member 32 of the medicament vial assembly in the manner best seen in FIG. 25. As the cannula pierces the septum, or member 32, a fluid flow path will be opened between the medicament reservoir of the vial and the outlet port 128 of cap assembly 124 permitting the medicament to flow from the reservoir, through the flow control means of the invention and then outwardly of the apparatus through a conduit 163 which is connected to the outlet 128 of the cap assembly in the manner shown in FIG. 25. As the medicament vial moves to the right, elastomeric spacer plug 138 will once again be compressed from the expanded configuration shown in FIG. 24 to the compressed configuration shown in FIGS. 25 and 28.

Figure 28:
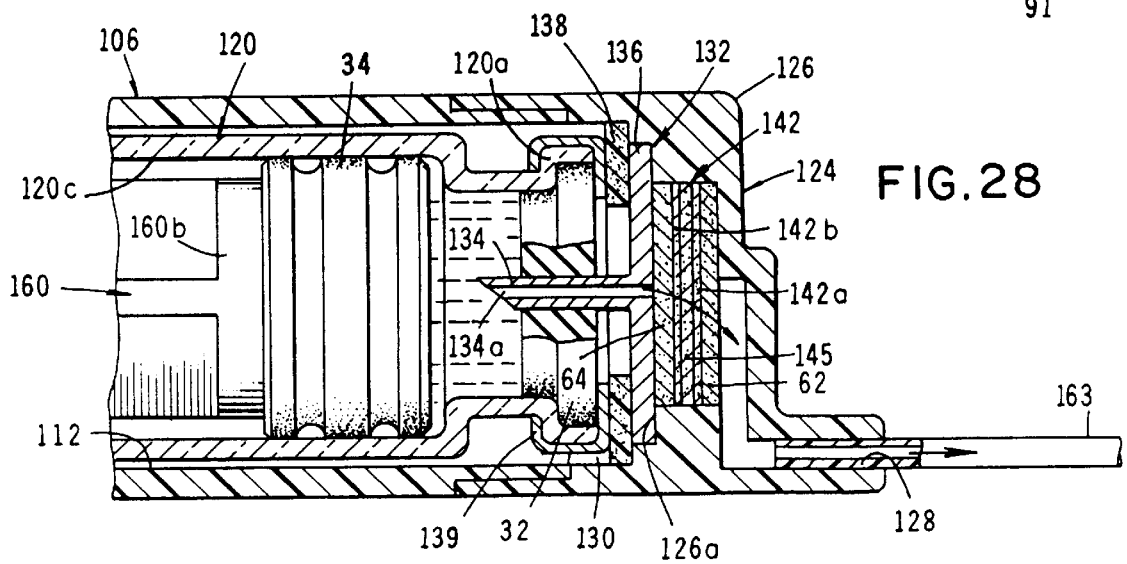
FIG. 28 is an enlarged, fragmentary, cross-sectional view of the dispensing end of the apparatus as shown in FIG. 25.
Figure 41:
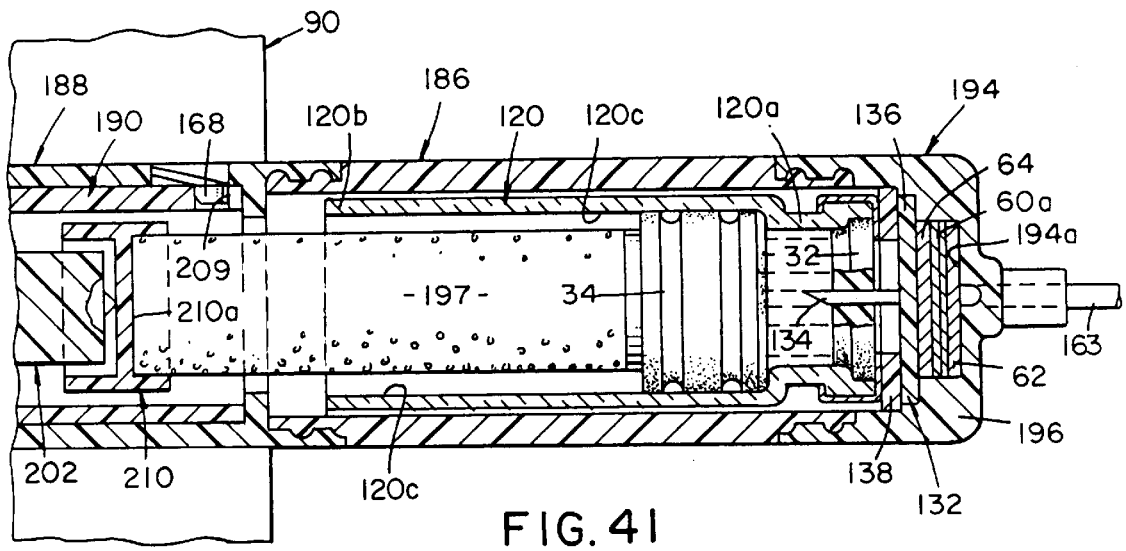
FIG. 41 is a cross-sectional view taken along lines 41—41 of FIG. 40.
Figure 42:
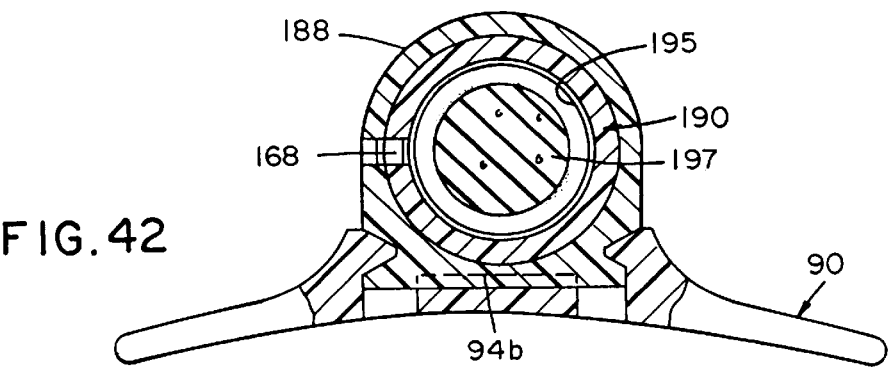
FIG. 42 is a cross-sectional view taken along lines 42—42 of FIG. 40.

After fluid flow path between reservoir 120c and outlet 128 is open, the stored energy source, or elastomeric member 123 is free to move from a more compressed to a less compressed configuration. This causes plunger 160 to move axially of reservoir 120c from a first position shown in FIG. 24 to a second position shown in FIGS. 25 and 28. As the plunger moves within the reservoir, the fluid contained therein will be urged into the fluid passageway 134a of cannula 134 and toward the flow control means of the apparatus (FIG. 28). As can be observed in FIG. 28, septum, or piercable member 32, is retained within the vial by a crimp cap 139. The fluid will then flow through rate control assembly 142, outwardly of outlet 128 and into conduit 163 for dispensing to a patient as appropriate.

Referring now particularly to FIGS. 16 and 23, it is to be noted that the body portion 110 of the operating member is provided with an aperture 166 proximate its inboard end, while body portion 108 is provided with a cooperating, spring-loaded detent assembly 168. Detent assembly 168 and aperture 166 comprise the locking means of this form of the invention for locking operating member 110 to body portion 108. More particularly, as member 110 moves into seating engagement with member 108, detent assembly 168 will move into aperture 166 in the manner shown in FIG. 26 thereby effectively preventing removal of the operating member once it has been seated.

Turning next to FIGS. 14, 16, 19, 21, and 24, it can be seen that, as before, the present embodiment of the invention comprises a support means for removably supporting body 102. This support means is of identical construction to that previously described and operates in the same manner. Accordingly, the details of construction of the support means or base assembly 90 will not be here repeated.

Referring next to FIGS. 29 through 43 of the drawings, still another form of the dispensing apparatus of the present invention is there illustrated and generally designated by numeral 182. The apparatus of this alternate form of the invention is similar in several respects to the previously described embodiments of the invention and like numbers have been used in FIGS. 29 through 43 to identify like components.

As seen in FIGS. 31 and 35, the apparatus of this latest form of the invention comprises an elongated body 184, which is, once again, made up of three interconnected, generally tubular shaped portions 186, 188, and 190 respectively, portion 190 once again comprising a part of the operating means of the invention. As best seen by referring to FIG. 39, when portions 186, 188, and 190 are interconnected to form elongated body 184, they define first, second and third communicating interior chambers 191, 193, and 195 respectively.

Removably receivable within first chamber 191 is a prefilled medicament vial 120 of the general character previously described having a first end 120a sealed by a piercable member 32 (FIG. 41) and a second end 120b sealed by an elastomeric plunger 34 which is telescopically movable longitudinally of the internal fluid reservoir of chamber 120c of vial 120. As before, pierceable member 32 comprises a part of the outlet means of the reservoir for permitting fluid flow therefrom.

Unlike the previously described embodiments of the invention, in the present form of the invention, the plunger engaging means for moving plunger 34 of the vial assembly has been eliminated and movement of the plunger of the vial assembly is accomplished in a different manner presently to be described.

Disposed within second chamber 193 of the elongated body is yet another form of the important stored energy means of the invention, which means provides the energy to move plunger 34 within the vial assembly. This unique stored energy means here comprises a generally cylindrically shaped elastomeric plug 197 which is movable from a first configuration shown in FIG. 39 to a second, deformed configuration wherein it has a tendency to uniformly return toward its first configuration.

As before, the apparatus of this latest form of the invention includes flow control means for controlling the outward flow of fluid flowing from the reservoir or internal chamber 120c of vial 120. The flow control means is essentially identical to that shown in FIG. 43, but here comprises an end cap assembly 194 which is threadably interconnectable with body portion 186 rather than being bonded thereto. As best seen by referring to FIGS. 41 and 43, cap assembly 194 comprises a hollow cap 196 having a fluid outlet 128 (FIG. 43) and defining an interior chamber 198. Disposed within chamber 198 and forming a part of the flow control means of the invention is a cannula assembly 132 which comprises a hollow cannula 134 and a cannula support plate 136. As before, cannula 134 can be either a conventional, sharp hollow needle or a blunt end cannula of a character well known in the art. Cannula assembly 132 is bonded in position within cap 196. A compressible, elastomeric spacer plug 138 which is receivable within the mouth of cap chamber 198 in the manner shown in FIG. 39. As before, spacer plug 138 initially maintains spacing between the cannula and piercable member 32 until plunger 34 is forcefully acted upon by the stored energy means. Prior to the cap assembly being interconnected with body portion 186, interior chamber 198 of the cap assembly is closed and maintained in the sterile configuration by a tear-away cap 140 (FIGS. 31 and 32).

Disposed between cannula support plate 136 and an end wall 194a (FIG. 39) of cap 194 is flow control means for controlling fluid flowing outwardly through outlet 128 of cap 196. This fluid rate control means is similar to that described in connection with FIGS. 1 through 5, but includes a combination filter and rate control laminate 60a which functions to control the rate of flow of fluid outwardly of the device. Laminate 60a comprises wafers similar in construction to previously described wafers 142a and 142b.

Turning next to FIGS. 29, 30, 31, 35 and 40, it is to be noted that operating member 190 of this latest form of the invention includes a unit condition indicator means for indicating that the apparatus has been placed into an operational condition. This indicator means here comprises an indicator element 202 which is carried within finger-engaging portion 190a of operating member 190. Element 202 includes an elongated, cylindrical body 202a, an enlarged diameter portion 202b, a circumferentially extending groove 202c disposed proximate portion 202b (FIG. 35) and a head portion 202d. Portion 202d is telescopically receivable within an opening 204 of member 190. Resiliently deformable locking tabs 204a are provided in opening 204 for locking engagement with groove 202c when the indicator is in the extended position shown in FIG. 39.

In using the apparatus of the invention shown in FIGS. 29 through 43, the component parts of the apparatus are assembled in the manner previously described and as shown in FIG. 35. As before, the body 190 of the operating member is provided with threads 206 (FIG. 31) which engage internal threads 208 that are formed internally of second body portion 188 (see also FIG. 39). Prior to use of the device, member 190 is connected to but not fully threaded into body portion 188. When initially connected, the operating member extends outwardly from body portion 188 in the manner shown in FIGS. 39 and 40. As before, to protect threads 206, a frangible covering 76 is placed around body portion 190 in the manner shown in FIGS. 29 and 35.

After the apparatus has been assembled in the manner shown in FIGS. 30 and 35, and prior to its being used, covering 76 is removed from body portion 190 in the manner depicted in FIG. 29. This done, cap portion 190 is threadably advanced inwardly of body portion 188 in the manner illustrated in FIGS. 33 and 39. Turning to FIG. 40, it is to be noted that elongated body portion 202*a* of the indicator element is in engagement with one face of the central wall 210*a* of a generally cylindrically shaped guide member 210. The other face of wall 210*a* is maintained in engagement with elastomeric member 197 so that as member 190 is threaded into body portion 188 elastomeric member 197 will be controllably deformed. As operating member 190 moves toward a seated position, head portion 202*d* of indicator element 202 will move from the retracted position shown in FIG. 35 to the extended position shown in FIG. 39. As the indicator element moves to its fully extended position, resiliently deformable tabs 204*a* will move into groove 202*c* so as to lock the indicator element in the fully extended position (see FIGS. 39 and 40). Additionally, because of the resistance offered by the fluid within the vial reservoir to axial movement of plunger 34, vial assembly 120 will be moved to the right as viewed in FIG. 40 causing the compression of elastomeric spacer 138 and simultaneously causing cannula 134 to pierce piercable member 32 of the medicament vial assembly in the manner best illustrated in FIG. 43. As the cannula pierces the septum, or member 32, a fluid flow path will be opened between the medicament reservoir of the vial and the outlet port 128 of cap assembly 194 permitting the medicament to flow from the reservoir, through the flow control means of the invention and then outwardly of the apparatus through a conduit 163 which is connected to the outlet 128 of the cap assembly in the manner shown in FIG. 43. As before, upon movement of the medicament vial to the right, elastomeric spacer plug 138 will be compressed.

Figure 43:
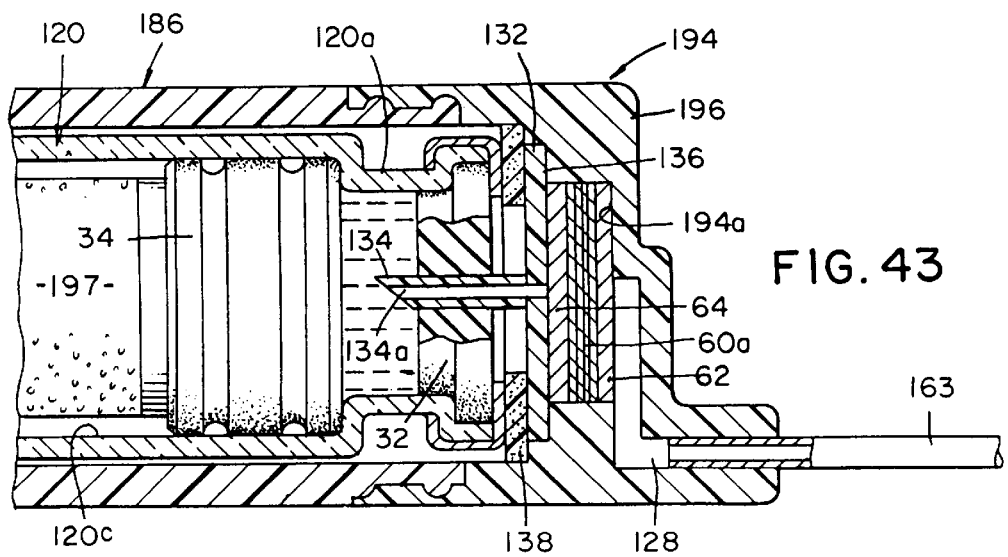
FIG. 43 is an enlarged, fragmentary, cross-sectional view of the dispensing end of the apparatus as shown in FIG. 41.

After the fluid flow path between reservoir 120*c* and outlet 128 is open, the stored energy source, or elastomeric member 197 is free to move toward its initial starting configuration. Engagement of plunger 34 by the inboard end of elastomeric member 197 will cause plunger 34 to move axially of reservoir 120*c* from a first position shown in FIG. 36 to a second position shown in FIGS. 40 and 41. As the plunger moves within the reservoir, the fluid contained therein will be uniformly urged into the fluid passageway 134*a* of cannula 134 and toward the flow control means of the apparatus (FIG. 43). The fluid will then flow through rate control assembly 60*a*, outwardly of outlet 128 and into conduit 163.

Referring now particularly to FIGS. 31 and 36, it is to be noted that member 190 is provided with an aperture 209 proximate its inboard end, while body portion 188 is provided with a spring-loaded detent assembly 168. Detent assembly 168 is of the character previously described and comprises the locking means of this latest form of the invention for locking member 190 to body portion 188. As member 190 moves into seating engagement, detent assembly 168 will move into locking engagement within aperture 209 in the manner shown in FIG. 41 thereby effectively preventing removal of the operating member once it has been seated.

This latest embodiment of the invention also includes a support means for removably supporting body 182. This support means is of identical construction to that previously described and operates in the same manner. Accordingly, the details of construction of the support means or base assembly will not be here repeated.

Turning to FIGS. 44 through 55 of the drawings, yet another form of the dispensing apparatus of the present invention is there illustrated and generally designated by numeral 222. The apparatus of this alternate form of the invention is similar in some respects to the previously described embodiments of the invention and like numbers have been used in FIGS. 44 through 55 to identify like components.

The apparatus of this latest form of the invention comprises an elongated body 224, which is made up of four interconnected, generally tubular shaped portions 226, 228, 230, and 232 respectively, the operating means of the invention being generally designated as 242 (FIG. 48). Portions 226, 228, 230, and 232 are interconnected to form elongated body 224 and, when interconnected, define first, second, third and fourth communicating interior chambers 233, 234, 235 and 236 respectively.

Removably receivable within first chamber 233 is a prefilled medicament vial 120 of the character previously described having a first end 120*a* sealed by a piercable member 32 (FIG. 48) and a second end 120*b* sealed by an elastomeric plunger 34 which is telescopically movable longitudinally of the internal fluid reservoir of chamber 120*c* of vial 120. As before, pierceable member 32 comprises a part of the outlet means of the reservoir for permitting fluid flow therefrom. Receivable within second chamber 234 of elongated body 224 is plunger engaging means, or displacement piston 240 for moving plunger 34 of the vial assembly axially of chamber 120*c*. The details of construction and operation of displacement piston 240 will presently be described.

Figure 46:
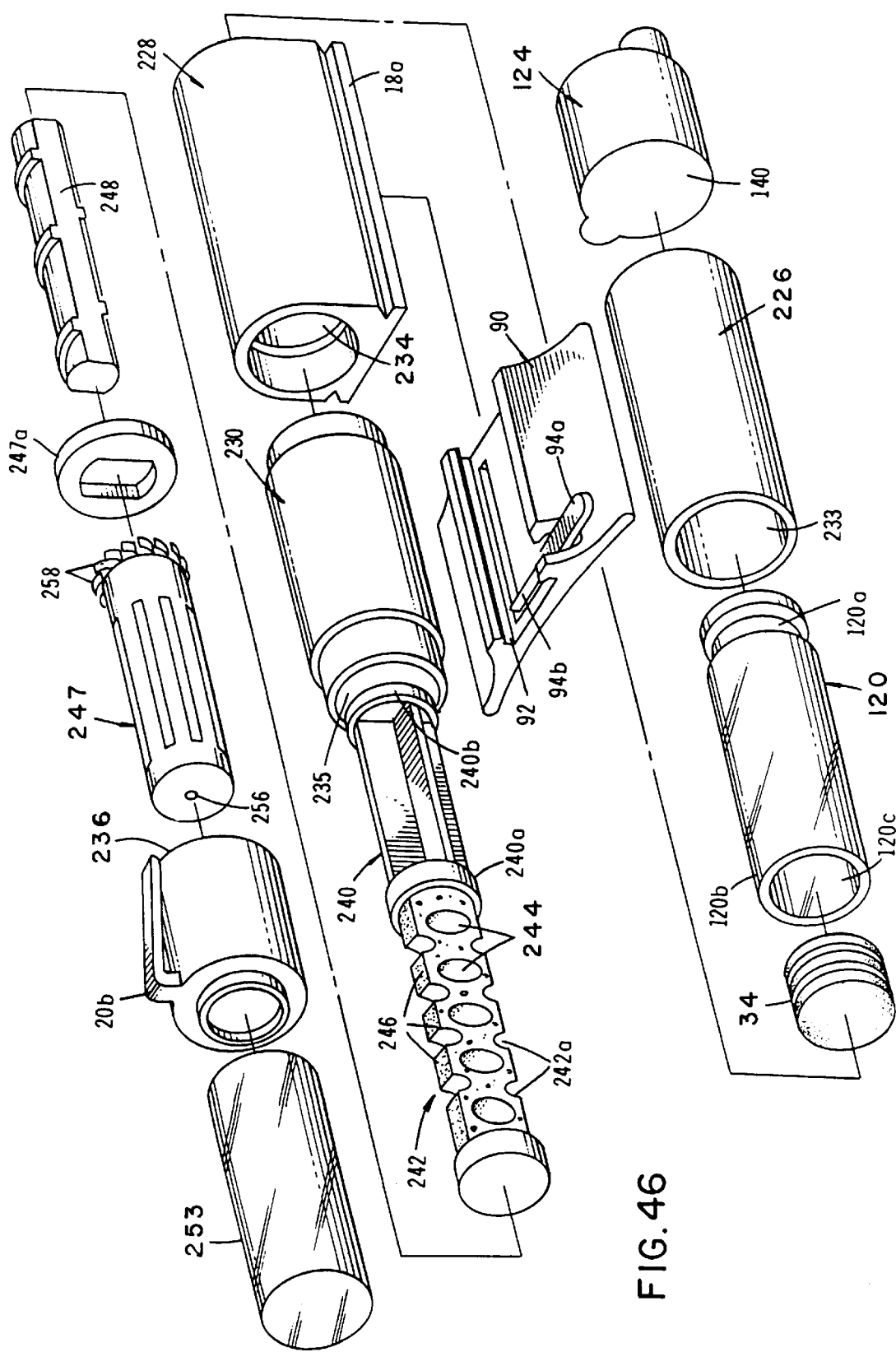
FIG. 46 is a generally perspective, exploded view of the apparatus of FIG. 44.

Disposed within third chamber 235 of the elongated body is a slightly different form of stored energy means of the invention, which functions to operate displacement piston 240. This unique stored energy means here comprises an elongated, substantially flat member 242 which is provided with a plurality of longitudinally spaced, oval shaped apertures 244. Member 242 is movable from a substantially undeformed condition shown in FIG. 48 to a second, more compressively deformed configuration wherein it has a tendency to return toward its first configuration. It should be understood that in some circumstances, it may be desirable to partially load, deform, or compress the stored energy means depending upon the materials used and the flow curve desired. As best seen in FIG. 46, member 242 also has a plurality of longitudinally spaced apart grooves and ridges 242*a* and 242*b* respectively. Member 242 can be constructed from materials of the character previously described herein and may be constructed from a polymer foam.

The apparatus of this latest form of the invention also includes flow control means for controlling the outward flow of fluid following from the reservoir or internal chamber 120*c* of vial 120. The flow control means of this embodiment is similar in construction and operation to the flow control means of the previously described embodiment and the details of its construction will not be repeated here.

Turning particularly to FIGS. 44, 46, 48 and 55, it is to be noted that the operating means of this latest form of the invention is of a substantially different construction than that previously described herein. More particularly, portion 232 here rotatably supports a finger-engaging housing, which is controllably rotated to place the apparatus into a flow discharge condition. In this latest form of the invention the operating means comprises an internally threaded, rotatable, finger-engaging housing 247 and a cooperating, externally threaded control rod 248, a portion of which is receivable within third body portion 230 as the apparatus is placed in the flow discharge mode (see FIG. 55). Disposed within member 232 is a retaining ring 247a to which the forwardly extending finger-engaging housing 247 is connected. Also supported by cap portion 232 is a transparent, tubular cover 253, which, as best seen in FIG. 48, encapsulates housing member 247.

After the apparatus has been assembled in the manner shown in FIGS. 46 and 48, a cup-shaped head portion 240a of member 240 will engage elastomeric member 242. Simultaneously end 240b of member 240 will engage plunger 34 of the vial assembly in the manner shown in FIG. 48. In operating the apparatus of this latest embodiment, cover 253 is initially removed and finger-engaging housing 247 is rotated using the fingers of the operator. Rotation of housing 247 relative to member 232 will cause control rod 248 to move from the starting position shown in FIG. 48 to the extended position shown in FIG. 55. As control rod 248 moves toward its extended position, it will tend to controllably compress elastomeric member 242. Member 242 will, in turn, exert a longitudinal force on displacement piston 240. However, because of the resistance offered by the fluid within the vial reservoir to axial movement of plunger 34, the displacement piston will cause vial assembly 120 to move to the right as viewed in FIG. 55 resulting in the compression of elastomeric spacer 138 and simultaneously causing cannula 134 to pierce piercable member 32 of the medicament vial assembly in the manner best illustrated in FIG. 55. As the cannula pierces the septum, or member 32, a fluid flow path will be opened between the medicament reservoir of the vial and the outlet port 128 of cap assembly 124 accommodating fluid flow from the reservoir, through the flow control means of the invention and then outwardly of the apparatus through a conduit 163 which is connected to the outlet 128 of cap assembly by a standard connector, such as a luer connector 163a in the manner shown in FIGS. 48 and 55. As before, when the medicament vial moves to the right, elastomeric spacer plug 138 will be compressed from its expanded configuration to its compressed configuration allowing the cannula to pierce septum 32.

After the fluid flow path between reservoir 120c and outlet 128 is open, the stored energy source, or elastomeric member 242, is free to return toward its initial starting configuration. This causes plunger 34 to move axially of reservoir 120c from a first position shown in FIG. 48 to a second position shown in FIG. 55. As the plunger moves within the reservoir, the fluid contained therein will be uniformly urged into the fluid passageway 134a of cannula 134 and toward the flow control means of the apparatus (FIG. 48). the fluid will then flow through rate control assembly 142, outwardly of outlet 128 and into conduit 163.

Figure 50:
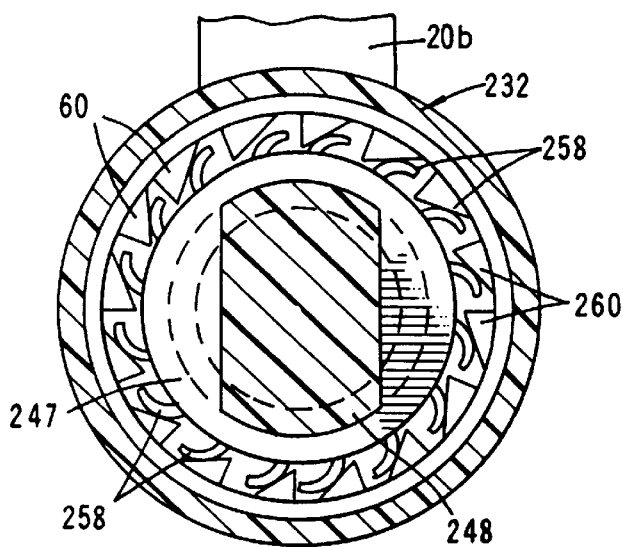
FIG. 50 is a cross-sectional view taken along lines 50—50 of FIG. 48.
Figure 51:
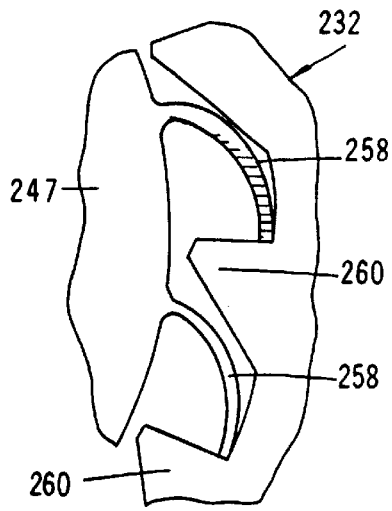
FIG. 51 is an enlarged, fragmentary view showing the manner in which the locking tabs of the device interlock with the locking teeth.
Figure 53:
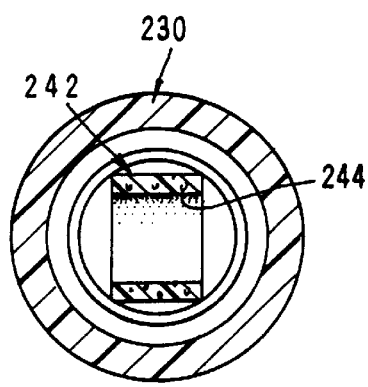
FIG. 53 is a cross-sectional view taken along lines 53—53 of FIG. 48.
Figure 52:
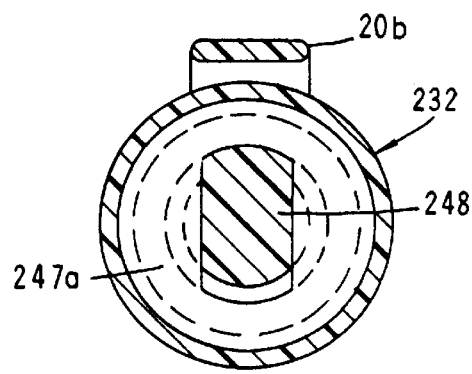
FIG. 52 is a cross-sectional view taken along lines 52—52 of FIG. 48.
Figure 54:
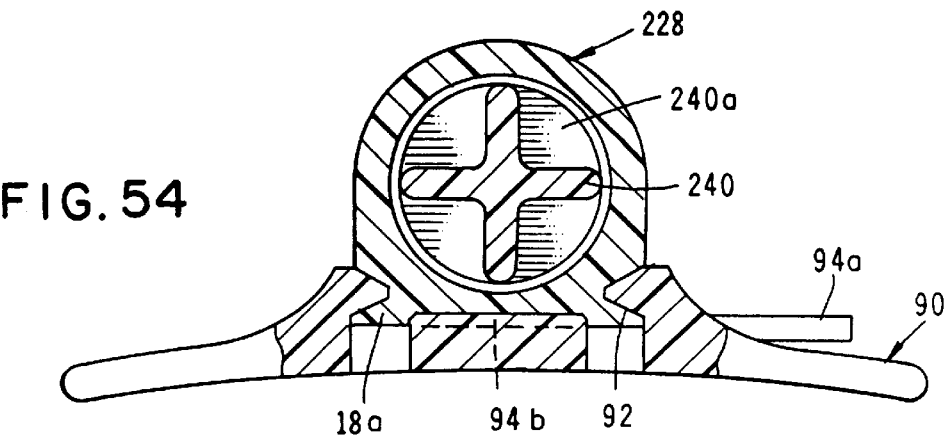
FIG. 54 is a cross-sectional view taken along lines 54—54 of FIG. 48.

Referring now particularly to FIGS. 48 and 55, it is to be noted that member 247 is provided with a vent aperture 256 and includes proximate its inboard end a plurality of circumferentially spaced locking tabs 258 which lockably engage circumferentially spaced teeth 260 provided internally of portion 232 (see also FIGS. 50 and 51). Tabs 258 and teeth 260 comprise the locking means of this latest form of the invention for preventing counter rotation of housing 247. With this construction, once control rod 248 has been fully advanced counterclockwise or loosening rotation of the finger-engaging housing is positively prevented.

Turning next to FIGS. 56 through 67 of the drawings, still another form of the dispensing apparatus of the present invention is there illustrated and generally designated by numeral 272. The apparatus of this alternate form of the invention is also similar in certain respects to the previously described embodiments of the invention and like numbers have been used in FIGS. 56 through 67 to identify like components.

The apparatus of this latest form of the invention, like the embodiment just described, comprises an elongated body 274, which is made up of four interconnected, generally tubular shaped portions 276, 278, 280, and 282 respectively, a portion of the operating means of this form of the invention being designated as 282 (FIG. 56). These portions are interconnected to form elongated body 274 and, when interconnected, define first, second, third and fourth communicating interior chambers 284, 286, 288 and 290 respectively (FIG. 60).

Figure 60:
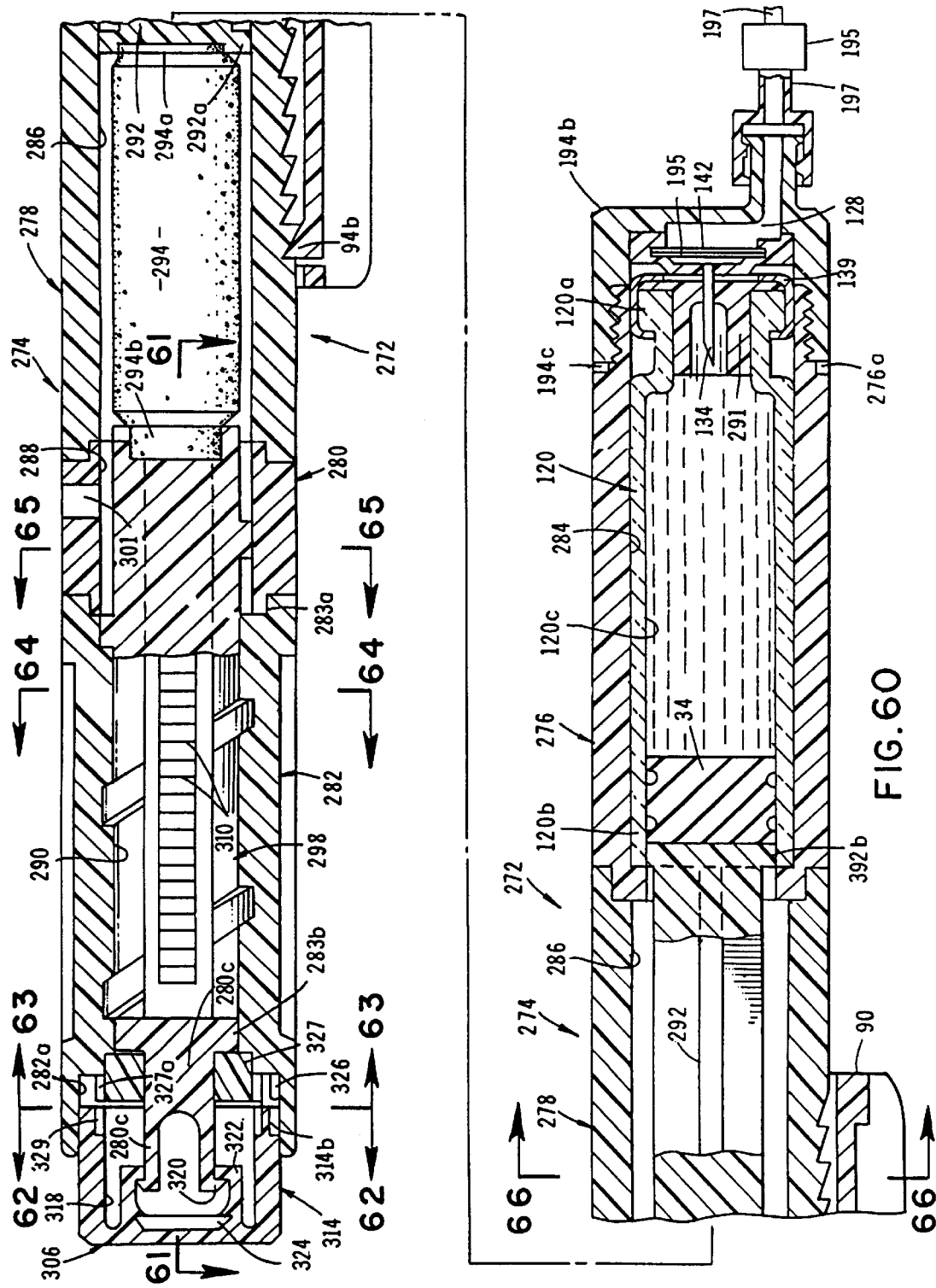
FIG. 60 is a cross-sectional view taken along lines 60—60 of FIG. 59.

Removably receivable within first chamber 284 is a prefilled medicament vial 120 of the character previously described having a first end 120a sealed by a pierceable member 291 which is retained in position by a crimp cap 139 (FIG. 60). Vial 120 also has a second end 120b which is sealed by an elastomeric plunger 34 which is telescopically movable longitudinally of the internal fluid reservoir of chamber 120c of vial 120.

Receivable within second chamber 286 of elongated body 274 is plunger engaging means, or push rod 292 for moving plunger 34 of the vial assembly axially of chamber 120c. The details of construction and operation of push rod 292 will presently be described.

Disposed within second chamber 286 of the elongated body is yet another form of stored energy means of the invention, which functions to operate push rod 292. This unique stored energy means here comprises an elongated, generally cylindrically shaped member 294 which includes reduced diameter end portions 294a and 294b. As before, member 294 is movable from a first configuration to a second, more deformed configuration wherein it has a tendency to controllably return toward its initial configuration. While member 294 can be constructed from any of the materials previously described in connection with the embodiment of the invention shown in FIGS. 1 through 5, it is here constructed from a polymer foam material having special uniaxial compression characteristics.

The apparatus of this latest form of the invention also includes flow control means for controlling the outward flow of fluid following from the reservoir or internal chamber 120c of vial 120. The flow control means of this embodiment is very similar in construction and operation to the flow control means of the embodiment shown in FIGS. 30 through 43, save that the end cap, here designated as 194b, is provided with circumferentially spaced locking teeth 194c which lockably engage yieldably deformable tabs 276a provided on body portion 276. Additionally, the distribution plates have here been eliminated and filter means, here shown as a microporous filter 295 for filtering particulate matter from the fluid flowing under pressure through cannula 134, is disposed adjacent the rate control member 142 (FIG. 60). Filter 295 is of a character well known to those skilled in the art and can be constructed from various readily available materials such as polysulfone, and polypropylene wafers having a porosity of between 0.8 and 1.2 microns. When the locking tabs 276a engage teeth 194c in the manner shown in FIG. 60 removal of cap 194b is prevented. It is also to be noted that, if desired, the septum of the medicament vial can be penetrated by the cannula of the flow control means during connection of the end cap 194b to body portion 276 rather than using the operating means to cause penetration of the septum by the cannula.

Turning particularly to FIGS. 56, 58, 60 and 67, it is to be observed that this latest form of the invention is of a substantially different construction than that previously described herein and includes a number of special features not found in the previously described embodiments. For example, this latest form of the invention includes different and quite novel operating means for placing the apparatus into an armed, operational condition, that is a condition wherein the stored energy means is placed under load deformation. More particularly, the operating means here includes tactile sensing means that permits the user to tactilely sense the advance of the control rod portion of the operating means during the loading step. Additionally, the device includes novel indicator means for indicating the extent of advancement of the control rod during the loading step.

The novel operating means here comprises, in addition to the externally threaded control rod 298, an internally threaded finger-engaging means here comprising the previously identified body portion 282. As indicated in FIG. 67, as member 282 is rotated, it cooperates with threaded control rod 298 to strategically advance the control rod into third body portion 280. Disposed intermediate finger-engaging housing 282 and body portion 278 is the previously identified indicator means which here comprises tubular body portion 280. Body portion 280 is provided with a viewing window 301 that permits the user to view a colored strip 302 of various selected colors (FIG. 58) that extends longitudinally of control rod 298. The operation of the indicator means as well as the operation of the novel locking means of this latest form of the invention will presently be described in greater detail.

After the apparatus has been assembled in the manner shown in FIG. 60, a cup-shaped head portion 292*a* of push rod 292 will engage portion 294*a* of elastomeric member 294. Simultaneously, end 292*b* of the push rod will engage plunger 34 of the vial assembly in the manner shown in FIG. 60. At the start of the operation of the apparatus of this latest embodiment, locking means, shown here as a push button assembly 306, is in the unlocked configuration shown in FIG. 60. With the locking means in this unlocked position, rotation of member 282 relative to member 280 and relative to control rod 298 will cause control rod 298 to advance from the starting position shown in FIG. 60 to the extended position shown in FIG. 67.

Figure 58:
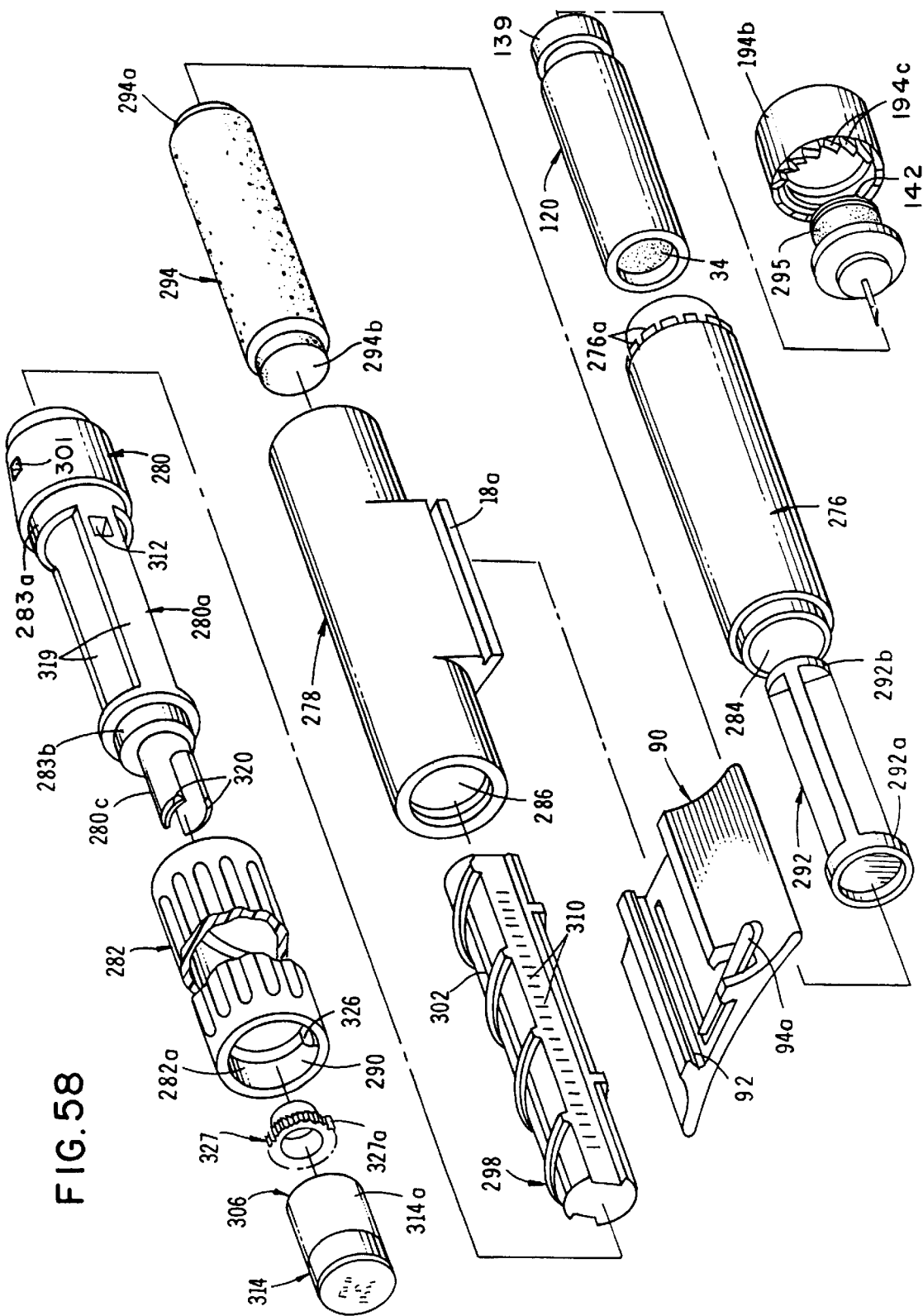
FIG. 58 is a generally perspective, exploded view of the apparatus shown in FIG. 56.

As best seen in FIGS. 58, 60, and 61, control rod 298 includes a plurality of longitudinally spaced splines 310 which, during operation, are sequentially engaged by an interiorly extending tab 312 (FIGS. 58 and 60) provided on a forwardly extending portion 280*a* of member 280. Splines 310 and tab 312 comprise the tactile sensing means of the invention. It is also to be noted that portion 280*a* includes spaced apart bearing surfaces 283*a* and 283*b* upon which the finger-engaging member 282 rotates (FIGS. 58 and 60). With this construction, as tab 312 engages splines 310, a tactile sensation will be imparted to the user as the user rotates finger-engaging member 282.

As before, as the control rod 298 moves toward its advanced or extended position, it will controllably compressively deform elastomeric member 294. Member 294 will, in turn, exert a longitudinal force on push rod 292. However, when the outlet port of cap 194*b* communicates with a valving means, such as a valve 195 in the manner shown in FIG. 60, the valve means can be used to control fluid flow outwardly of the outlet port. Accordingly, when the valve is closed, the resistance offered by the fluid within the vial reservoir to axial movement of plunger 34 will cause the controlled compression of elastomeric member 294. With this construction, upon opening valve 195, only then will a fluid flow path be formed between the medicament reservoir of the vial and a dispensing conduit 197, which is connected to the outlet of the valve in the manner shown in FIG. 67, thereby permitting fluid to be dispensed from the device. As before, expansion of the stored energy means provides the force necessary to cause the controlled movement of the vial plunger and the resulting discharge of the fluid contained within the vial.

As the control rod advances within body portion 280 the colored indicator strip 302 which is visible through viewing window 301 of the indicator means will indicate to the user the stage of loading of the stored energy means. It should be understood that, this indicator strip can be provided with indicia indicating the extent of linear displacement of the control rod. Under certain circumstances, it may be desirable to provide differential loading of the stored energy means so that alternate flow rates can be selectively achieved. To lock the control rod in the extended position, push button 314 of the locking means or locking assembly 306 is pushed inwardly into the open end 282*a* of body portion 282. End surface 314*a* is colored to easily show the condition of the device. As best seen by referring to FIG. 60, push button 314 includes an internal chamber 318 into which a generally cylindrically shaped extension 280*c* of portion 280*a* of member 280 extends. As best seen in FIG. 58, portion 280*a* comprises a pair of spaced apart connector arms 319 which connect portions 283*a* and 283*b*. In the present form of the invention, extension 280*c* not only rotatably supports finger-engaging member 282, but also uniquely forms a part of the locking means of the invention.

Formed on extension 280*c* are circumferentially spaced, arcuate shaped retaining segments 320 which are lockably engageable with a first annular collar 322 formed within chamber 318. Also formed within chamber 318 is a second annular collar 324 which is engagable by arcuate retaining segments 320 when push button 314 is pushed inwardly of body portion 282. To guide travel of push button 314 inwardly of body portion 282 and to lock the finger-engaging means against rotation with respect to member 280, the push button is provided with a keyway 314*a* (FIGS. 60 and 61) which slidably receives a key 326 formed within interior chamber 290 of body portion 282. Also forming a part of the locking means of this form of the invention, is a non-rotatable locking ring 327 which is affixed to extension 280*c* as by sonic bonding. As indicated in FIG. 58, ring 327 is provided with circumferentially extending teeth 327*a* which lockably engage serrations 329 provided within push button 314 when the push button is fully inserted as shown in FIG. 67. Because key 326 is locked within keyway 314*a*, rotation of the push button relative to the finger-engaging member is prevented. Therefore, when the push button is locked against rotation with respect to fixed ring 327, rotation of member 282 is also positively prevented.

As previously discussed, after the fluid flow path between reservoir 120*c* and conduit 197 is opened by opening valve 195, the stored energy source, or polymer foam member 292, is free to move toward its initial starting configuration. This causes plunger 34 to move axially of reservoir 120*c* from a first position shown in FIG. 60 to a second position shown in FIG. 67. As the plunger moves within the reservoir, the fluid contained therein will be urged into the fluid passageway 134*a* of cannula 134 and toward the flow control means of the apparatus (FIG. 67). The fluid will then flow under pressure through filter 295, through rate control assembly 142, and then outwardly of outlet 128 and into conduit 197 via valve 195.

Turning to FIG. 67A, an alternate form of the flow control means is shown. The alternate form is similar in many respects to that shown in FIG. 67, but further includes a fine bore cannula 199 disposed within the outlet passageway of the flow control cap. Cannula 199 functions to further control the rate of flow of fluid flowing outwardly of outlet 128. By varying the length and bore diameter of cannula 199, fluid flow rate can be precisely controlled. The fine bore cannula can be constructed of glass, plastic or metal and is preferably bonded in position within the flow control cap.

As before this latest embodiment of the invention also includes support means for removably supporting body 278. This support means is of identical construction to that previously described and operates in the same manner. This being the case, the details of construction of the support means will not be here repeated.

Referring now FIGS. 68 through 70 of the drawings, still another form of the dispensing apparatus of the present invention is there illustrated and generally designated by numeral 350. The apparatus of this alternate form of the invention is quite similar to the embodiment shown in FIGS. 55 through 67 and like numbers have been used in FIGS. 68 through 70 to identify like components.

The apparatus of this latest form of the invention, comprises an elongated body 352, which is made up of three interconnected, generally tubular shaped portions which house the medicament vial 120, the push rod 292, and the stored energy means, all of which are identical to those just described. However, the operating means of this form of the invention is of a different construction and the indicator means provided in the previous embodiment has been eliminated.

As before, the apparatus of this latest form of the invention includes flow control means for controlling the outward flow of fluid flowing from the reservoir or internal chamber 120c of vial 120. This flow control means is identical to that shown in FIGS. 55 through 67 and, therefore, will not here be described.

As indicated in FIG. 69, the operating means of this latest embodiment comprises an internally threaded finger-engaging means, shown here as body portion 354. Body portion 354 cooperates with a threaded control rod 356 to strategically advance the control rod into adjacent body portion 358. The locking means of this last form of the invention is also identical to that previously described. Accordingly, to lock control rod 356 in the fully advanced position, push button 314 of the locking means or locking assembly 316 is pushed inwardly into the open end 354a of body portion 354. As best seen by referring to FIG. 69, push button 314 includes an internal chamber 318 into which a generally cylindrically shaped extension 358a of body portion 358 extends. Extension 358a is similar to extension 280c of the previous embodiment and forms a part of the locking means of this latest form of the invention.

Formed on extension 358a of body portion 358 are arcuate retaining segments 360 which are engagable with a first collar 320 formed within chamber 318. Also formed within chamber 318 is a second set retention collar 324 which is engagable by retaining segments 360 when push button 314 is pushed inwardly of body portion 354. To guide travel of push button 314 inwardly of body portion 354 and to lock the finger-engaging means, or member 354, against rotation with respect to member 358, the push button is provided with a keyway 314a (FIG. 69) which slidably receives a key 364 formed within body portion 354. Also forming a part of the locking means of this form of the invention, is a non-rotatable locking ring 327 which is identical in construction and operation to that previously described. As before, ring 327 is provided with circumferentially extending teeth 327a which lockably engage serrations 329 provided within push button 314 when the push button is fully inserted into the locked position.

After the fluid flow path between the fluid reservoir and the dispensing conduit is opened by opening the control valve 195 (not shown here), the stored energy source, or elastomeric member 292 is, as before, free to move toward its initial starting configuration. This causes plunger 34 of the vial to move axially of fluid reservoir so that the fluid contained therein will be uniformly urged into the fluid passageway 134a of cannula 134 and toward the flow control means of the apparatus. The fluid will then flow through the filter and rate control assembly into the dispensing conduit.

The primary difference between this latest embodiment of the invention and that shown in FIGS. 55 through 67 resides in the novel and important configuration of the threads of the finger-engaging member 354 and of control rod 356. Turning particularly to FIG. 70, it is to be observed that the cooperating threads vary in pitch as the threads progress along the length of the cooperating threaded members 354 and 356. For example, as shown in FIGS. 69 and 70, proximate the forward end of the device, the pitch "A" of threads designated as 361 is relatively course, while the pitch "B" of threads designated as 363 is much finer. The result of this unique threaded configuration is that, as finger-engaging member 354 is rotated, control rod 356 will initially advance faster for a given rotation of the finger-engaging member than it will after a portion of the control rod has advanced into body portion 358. This, of course, causes a more rapid initial compression of elastomeric member 294 followed by a slower compression thereof as the control rod advances progressively further into body portion 358.

This ability to variably, or non-linearly, compress and displace the elastomeric stored energy source is important when certain special materials are used to form the stored energy means. For example, when certain elastomeric materials are used in the construction of the stored energy means, it is advantageous to initially deform the stored energy means at a rapid rate with minimal rotation of the operating member in order to achieve an optimum initial position on the stress-strain curve of the particular material. Continual rotation will provide further, more gradual displacement of the stored energy means due to the finer thread configuration. This enables the precise, reproducible displacement loading of the stored energy means so that alternative fluid flow rates can be achieved. It is apparent that by varying the pitch of the threads of the operating means, the stored energy source can be deformed in a variety of ways thereby enabling the device to be customized for a number of fluid dispensing regimens.

It is to be understood that the use of variable pitch threads is not limited to the construction shown in FIGS. 55 through 69, but can be employed in the design and construction of the operating means of any of the forms of the invention shown in the drawings and previously described herein.

Referring lastly to FIGS. 71 through 74, alternate forms of the invention are there shown. For example, the support means shown in FIG. 71 includes a supporting base assembly 370, which is designed to be lockably interconnected with and securely support elongated body 352. As in the earlier described embodiments, base assembly 370 has a curved base plate 372 and includes a longitudinally extending channel 374 which slidably receives the flange portion 352a of body 352. As flange 352a slides into groove 374, locking protuberance 352b formed on flange 352a will releasably lock the base assembly to body 352.

So that supporting base assembly 370 can be affixed to the body of the patient, such as the patient's arm, a layer of adhesive 376 is affixed to the undersurface of curved base plate 372. Adhesive layer 376 is covered by pealable, protectable covering 378 which be peeled away at time of use by gripping corner portion 378a.

In FIG. 72 there is shown a support means which includes a plastic assembly 380, which is also designed to be lockably interconnected with elongated body 352. Assembly 380 includes a flat base plate 382 which is provided with longitudinally extending channel 384 that slidably receives the flange portion 352a of body 352. As before, base plate 382 is adapted to be removably locked to body 352 by means of locking protuberance 352b provided on flange 352a. However, unlike assembly 370, base assembly 380 is designed to be interconnected with a section of the belt "B" of the user and includes a forward path-like member 386 which is connected to base plate 382 by a living hinge 388 that bias the outer end 386a of member 388 toward base plate 382.

Figure 73:
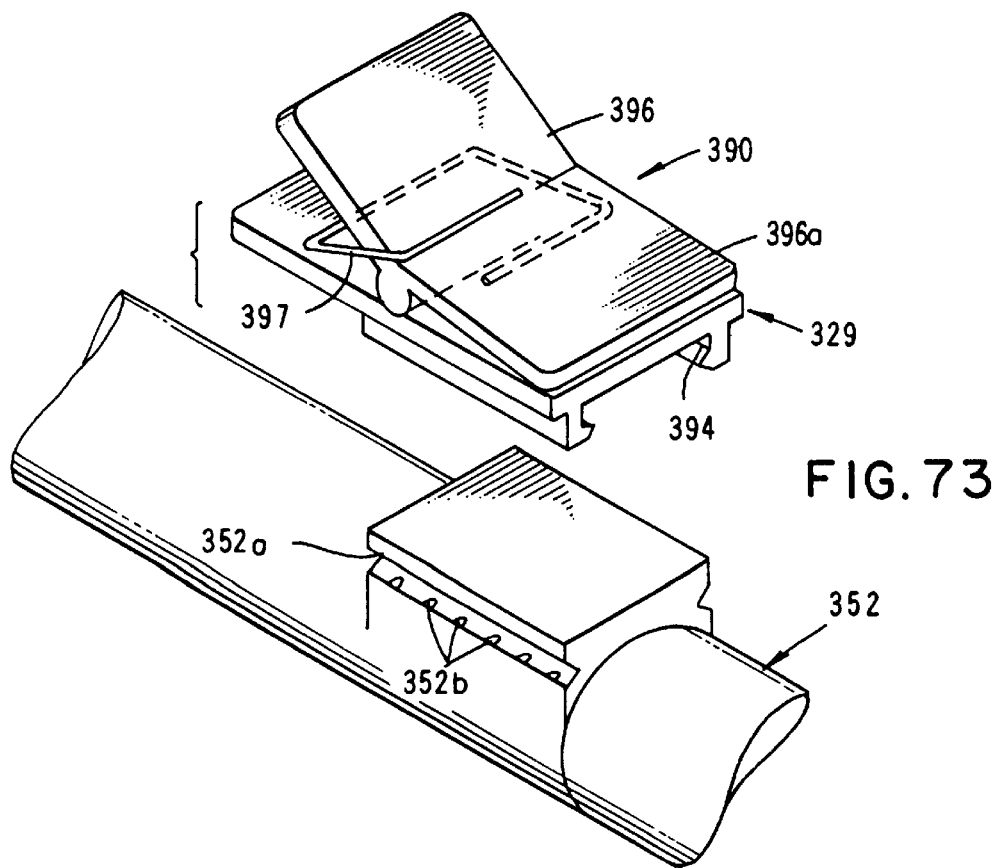
FIG. 73 is a generally perspective, exploded view of yet another form of supporting base shown here as comprising a spring loaded clip.

Referring to FIG. 73, the support means there shown includes a supporting base assembly 390, which is designed to be lockably interconnected with elongated body 352. Base assembly 390 includes a base plate 392 provided with a longitudinally extending channel 394 which slidably receives the flange portion 352a of body 352. As flange 352a slides into groove 394, locking protuberances 352b formed on flange 352a will releasably lock the base assembly to body 352.

So that supporting base assembly 390 can be clipped to the clothing of the patient, such as the patient's pajamas, a clip plate is pivotally connected to base plate 392 by biasing means shown where as a metal spring 397 which continuously urges edge portion 396a of clip plate 396 toward base plate 392 in the manner shown. Edge portion 396a can be moved away from plate 392 against the urging of spring 397 by pressing on edge portion 396b. With this construction, the apparatus of the invention can be conveniently clipped to and removed from the patient's clothing.

Figure 74:
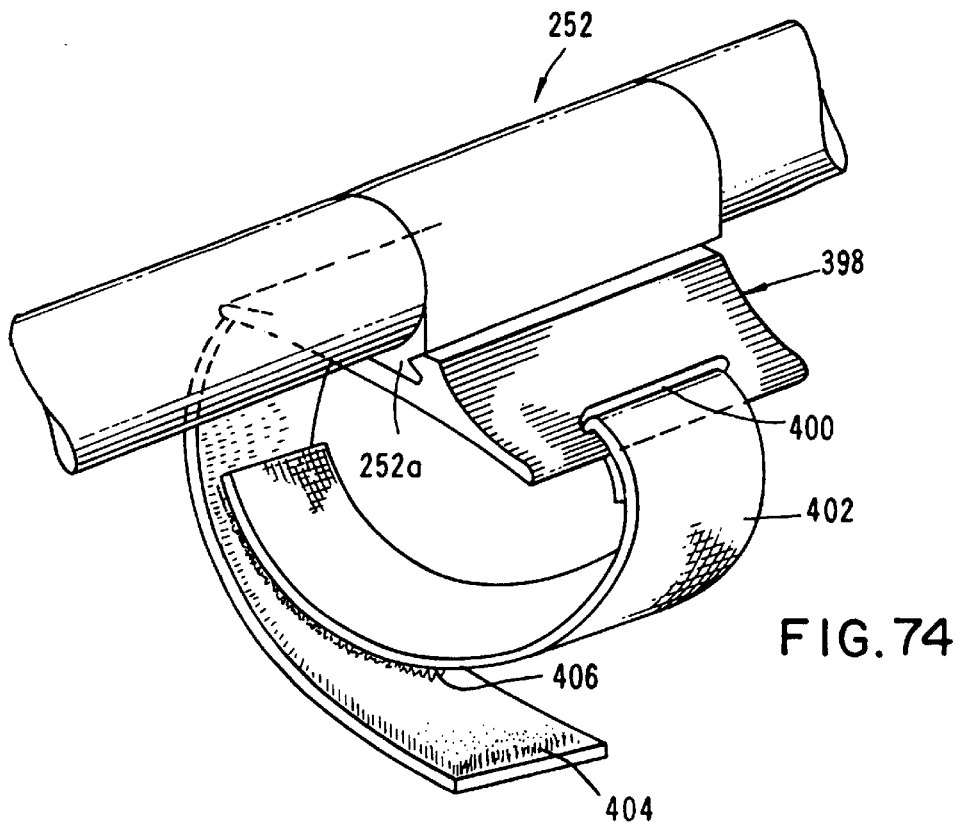
FIG. 74 is a generally perspective view of another form of supporting base to which a connector strap can be interconnected.

Turning now to FIGS. 74 the support means there shown is similar in construction to that shown in FIG. 56 and includes a supporting base assembly 398. Assembly 398 does not include the release arm 94a shown in FIG. 56, but rather includes longitudinally extending slots 400 on either side of the base plate which receive the ends of a connector strap 402 that can be secured in place around a patient's arm or leg and held in position by suitable means such as a hook and loop type connector material 404 and 406 of a character well known in the art.

With the construction shown in FIG. 74, supporting base assembly 398 can be quickly strapped to the patient's arm or leg and can travel with the patient beneath the patient's clothing if desired.

Having now described the invention in detail in accordance with the requirements of the patent statutes, those skilled in this are will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dispensing apparatus for dispensing fluids comprising:
   (a) a housing;
   (b) a fluid reservoir disposed within said housing, said reservoir having outlet means for permitting fluid flow from said fluid reservoir;
   (c) stored energy means for acting upon the fluid contained within said reservoir to cause the fluid to controllably flow through said outlet means, said stored energy means comprising a compressively deformable, elastomeric polymeric member carried by said housing, said compressively deformable, elastomeric polymeric member upon being compressively deformed expands substantially axially to cause fluid flow from said reservoir; and
   (d) operating means carried by said housing for controllably deforming said elastomeric polymeric member.

2. An apparatus as defined in claim 1 in which said elastomeric polymeric member is constructed from a flexible foam.

3. An apparatus as defined in claim 1 further including flow control means carried by said housing for controlling fluid flowing from said outlet means of said reservoir.

4. An apparatus as defined in claim 3 in which said fluid reservoir is formed by a prefilled vial receivable within said housing, said vial having first and second ends and a chamber within which a plunger is telescopically movable.

5. An apparatus as defined in claim 4 in which said reservoir outlet means comprises a penetrable sealing means for sealably closing said first end of said chamber.

6. An apparatus as defined in claim 5 in which said flow control means comprises a cannula connected to said housing for penetrating said penetrable sealing means.

7. An apparatus as defined in claim 6 in which said flow control means is provided with a fluid outlet port and further includes filter means for filtering particulates from fluid flowing from said reservoir outlet means and flow rate control means disposed between said cannula and said fluid outlet port for controlling the rate of fluid flow from said fluid outlet port.

8. An apparatus as defined in claim 7 in which said flow rate control means comprises a porous membrane.

9. A dispensing device for dispensing fluid comprising:
   (a) an elongated body having a plurality of interconnected chambers;
   (b) a fluid container receivable within one of said chambers, said fluid container having fluid outlet means and plunger means telescopically movable within said fluid container for urging fluid contained therein to flow out of said fluid outlet means;
   (c) fluid flow control means carried by said elongated body, said fluid flow control means having an outlet port in communication with said fluid outlet means of said container for controlling fluid flow from said outlet port; and
   (d) stored energy means disposed within one of said chambers for controllably moving said plunger means telescopically of said fluid container, said stored energy means comprising a polymeric elastomeric expandable member.

10. A device as defined in claim 9 further including operating means for controllably compressively deforming said expandable member.

11. A device as defined in claim 10 in which said operating means comprises an operating member rotatably carried by said elongated body.

12. A device as defined in claim 10 in which said elastomeric member comprises a flexible polymer foam.

13. A device as defined in claim 10 in which said fluid flow control means further comprises flow rate control means disposed between said fluid outlet means of said fluid container and said outlet portion of said flow control means for controlling the rate of fluid flow through said outlet port.

14. A device as defined in claim 10 in which said fluid flow control means further includes filter means for capturing particulates contained with the fluid flowing through said outlet of said fluid container.

15. A device as defined in claim 10 in which a first body portion of said elongated body is threaded and in which said fluid flow control means comprises a threaded cap threadably connected to said first body portion.

16. A device as defined in claim 10 in which said fluid container comprises a prefilled vial containing insulin, said vial having a first end sealed by a penetrable septum and a second end sealable by said plunger means.

17. A device as defined in claim 10 in which said expandable member comprises a generally cylindrically shaped polymeric latex plug.

18. A device as defined in claim 10 in which said expandable member comprises an elastomeric polymeric spring.

19. A device as defined in claim 10 in which said expandable member comprises an elongated member having a plurality of spaced-apart centrally disposed apertures.

20. A dispensing device for dispensing fluids at a controlled rate, comprising:
(a) an elongated body having first, second and third communicating chambers;
(b) a prefilled vial removably receivable within said first chamber of said elongated body, said vial having a first end sealed by a piercable member and a second end sealed by a plunger, said plunger being telescopically movable longitudinally of said vial;
(c) a plunger engaging means disposed within said second chamber of said elongated body for moving said plunger within said vial;
(d) stored energy means for operating said plunger engaging means, said stored energy means comprising a cellular polymeric mass disposed within said third chamber of said elongated body, said cellular polymeric mass being compressively deformable and having tendency to return toward a less deformed configuration; and
(e) operating means carried by said elongated body for controllably compressively deforming said cellular polymeric mass.

21. A device as defined in claim 20 further including support means for supporting said elongated body.

22. A device as defined in claim 20 further comprising flow control means connected to said elongated body for controlling fluid flow from said prefilled vial, said flow control means comprising a cannula for piercing said piercable member of said vial.

23. A device as defined in claim 22 in which said cellular polymeric mass has first and second ends, said first end being in engagement with said plunger engaging means and said second end being in engagement with said operating means.

24. A device as defined in claim 23 in which said operating means comprises an operating member rotatably carried by said elongated body.

25. A device as defined in claim 24 in which said elongated body includes a central portion defining said second chamber and in which said operating member defines said third chamber, said operating member being threadably connected to said central portion.

26. A device as defined in claim 25 further including locking means for lockably connecting said operating member to said central portion of said elongated body.

27. A device as defined in claim 25 in which said elongated body is threaded and in which said flow control means comprises a threaded flow control cap threadably interconnected with said elongated body.

28. A device as defined in claim 27 in which said flow control cap includes a fluid outlet port and in which said flow control means further includes a flow rate control membrane disposed within said flow control cap for controlling the rate of flow of fluid through said outlet port.

29. A device as defined in claim 28 in which said flow control means further includes distribution means disposed within said flow control cap for distributing fluid flowing from said cannula radially outwardly toward said flow rate control membrane.

30. A device as defined in claim 28 in which said flow control means further includes an infusion channel connected to said outlet port of said cap.

31. A device as defined in claim 28 in which said flow control means further includes a fine bore cannula disposed within said flow control cap for controlling the rate of fluid flow through said outlet port.

32. A dispensing apparatus for dispensing fluids comprising:
(a) an elongated housing;
(b) a fluid reservoir disposed within said housing, said reservoir having outlet means for permitting fluid flow from said fluid reservoir and including a plunger means movable within said reservoir for expelling fluid through said outlet means;
(c) stored energy means for moving said plunger means within said reservoir, said stored energy means comprising an expandable, elastomeric polymer disposed within said housing;
(d) flow control means connected to said housing for controlling fluid flow from said outlet means of said reservoir; and
(e) operating means for controllably compressively deforming said elastomeric polymer.

33. An apparatus as defined in claim 32 further including support means for supporting said housing, said support means including connector means for connecting said housing to the clothing of the user.

34. An apparatus as defined in claim 32 in which said stored energy means comprises an elongated shaped article receivable within said elongated housing.

35. An apparatus as defined in claim 34 in which said shaped article includes spaced apart grooves and ridges.

36. An apparatus as defined in claim 32 in which said flow control means is provided with a fluid outlet port and further includes flow rate control means disposed between said reservoir and said fluid outlet port.

37. An apparatus as defined in claim 36 in which said flow rate control means comprises a porous membrane.

38. An apparatus as defined in claim 36 in which said rate control means comprises a fine bore cannula.

39. An apparatus as defined in claim 32 further including support means for supporting said housing, said support means comprises a base having means for releasably connecting said housing thereto.

40. An apparatus as defined in claim 39 further including a strap means connected to said base for connecting said base to the user's body.

41. An apparatus as defined in claim 39 in which said means for releasably connecting said housing to said base comprises a multiplicity of upstanding locking ridges provided on said housing.

42. An apparatus as defined in claim 41 in which said connector means comprises a belt clip.

43. An apparatus as defined in claim 41 in which said connector means comprises a pajama clip.

44. A dispensing apparatus for dispensing injectable fluids, including antibiotics, oncolytics, analgesics and human growth hormones, said apparatus comprising:
   (a) a housing;
   (b) a fluid reservoir disposed within said housing, said reservoir having outlet means for permitting fluid flow from said fluid reservoir;
   (c) stored energy means for expelling fluid through said outlet means of said reservoir, said stored energy means comprising compressively deformable, expandable polymer disposed within said housing; and
   (d) operating means for controllably compressing said stored energy means.

45. An apparatus as defined in claim 44 in which said stored energy means comprises a compressively, flexible polymeric foam.

46. An apparatus as defined in claim 44 in which said stored energy means, upon being compressively deformed expands axially in a linear fashion.

47. An apparatus as defined in claim 44 in which said stored energy means, upon being compressively deformable, expands axially in a non-linear fashion.

48. An apparatus as defined in claim 44 in which said operating means compressively deforms said stored energy means at a substantially uniform rate.

49. An apparatus as defined in claim 44 in which said operating means compressively deforms said stored energy means at a non-uniform rate.

50. An apparatus as defined in claim 44 in which said operating means comprises an operating member operably associated with said stored energy means, said operating member being movable toward said stored-energy means at a controlled rate.

51. An apparatus as defined in claim 44 in which said operating means comprises an operating member, at least a portion of which is telescopically receivable within said housing.

52. An apparatus as defined in claim 44 in which said operating means comprises an elongated member having a threaded portion that is threadably receivable within said housing.

53. An apparatus as defined in claim 52 further including tactile sensing means for tactile sensing of the advance of said threaded portion within said housing.

54. An apparatus as defined in claim 52 in which said threaded portion of said operating member includes variable pitch threads.

55. An apparatus as defined in claim 52 further locking means for locking said operating means to said housing.

56. An apparatus as defined in claim 52 including indicator means for indicating the position of said threaded portion within said housing.

* * * * *